(12) United States Patent
Fujita et al.

(10) Patent No.: US 9,713,657 B2
(45) Date of Patent: Jul. 25, 2017

(54) CATHETER BALLOON AND BALLOON CATHETER

(71) Applicant: TERUMO KABUSHIKI KAISHA, Shibuya-ku (JP)

(72) Inventors: Yotaro Fujita, Shizuoka (JP); Makoto Onishi, Kanagawa (JP); Naoyuki Maeda, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 210 days.

(21) Appl. No.: 14/221,580

(22) Filed: Mar. 21, 2014

(65) Prior Publication Data
US 2014/0207171 A1 Jul. 24, 2014

Related U.S. Application Data

(63) Continuation of application No. PCT/JP2012/074419, filed on Sep. 24, 2012.

(30) Foreign Application Priority Data

Sep. 29, 2011 (JP) .................................. 2011-214496

(51) Int. Cl.
*A61M 29/00* (2006.01)
*A61L 29/06* (2006.01)
(Continued)

(52) U.S. Cl.
CPC .............. *A61L 29/06* (2013.01); *A61L 29/048* (2013.01); *A61M 29/02* (2013.01); *A61M 25/1029* (2013.01); *A61M 2025/1075* (2013.01)

(58) Field of Classification Search
CPC ....... A61M 2025/1075; A61M 25/1029; C08L 77/00; A61L 29/048; A61L 29/06; A61L 29/02; B29C 47/24; B29C 47/122
(Continued)

(56) References Cited

U.S. PATENT DOCUMENTS 5,879,369 A * 3/1999 Ishida .................. A61M 25/10
604/96.01
2005/0043459 A1 2/2005 Wang et al.
(Continued)

FOREIGN PATENT DOCUMENTS

CN 201132006 Y 10/2008
EP 0 768 097 A2 4/1997
(Continued)

OTHER PUBLICATIONS http://www.matbase.com/material-categories/natural-and-synthetic-polymers/engineering-polymers/material-properties-of-polyamide-11-nylon-11-pa-11.html#properties Accessed Jan. 11, 2016.*
(Continued)

*Primary Examiner* — Melanie Tyson
*Assistant Examiner* — Erich Herbermann
(74) *Attorney, Agent, or Firm* — Buchanan Ingersoll & Rooney PC

(57) ABSTRACT

A catheter balloon exhibiting improved pressure resistance of the entire membrane is formed of a membrane as a laminate of at least two layers including a polyamide elastomer layer and a polyamide layer, in which the polyamide elastomer layer is disposed at the inner side of the polyamide layer, a refractive index $n_{r1}$ in the circumferential direction of a cross-section perpendicular to the axis in the inner side surface of the polyamide layer is greater than a refractive index $n_{r2}$ in the circumferential direction of a cross-section
(Continued)

10 perpendicular to the axis in the inner side surface of the polyamide elastomer layer, and the difference between the refractive index $n_{r1}$ and the refractive index $n_{r2}$ is 0.01 or greater.

18 Claims, 8 Drawing Sheets

(51) Int. Cl.
*A61L 29/04* (2006.01)
*A61M 29/02* (2006.01)
*A61M 25/10* (2013.01)

(58) Field of Classification Search
USPC .......................................... 606/192, 195, 198
See application file for complete search history.

(56) References Cited

U.S. PATENT DOCUMENTS

| | | | |
|---|---|---|---|
| 2006/0085022 A1* | 4/2006 | Hayes | A61M 25/104 606/192 |
| 2006/0106413 A1* | 5/2006 | Bence | A61B 17/320725 606/192 |
| 2010/0130926 A1 | 5/2010 | Lee et al. | |

FOREIGN PATENT DOCUMENTS

| | | | | |
|---|---|---|---|---|
| JP | 09-38195 A | 2/1997 | | |
| JP | 2004-298363 A | 10/2004 | | |
| JP | 2005-246097 A | 9/2005 | | |
| JP | 2005-305187 A | 11/2005 | | |
| JP | 2005-319289 A | 11/2005 | | |
| JP | 2007-61258 A | 3/2007 | | |
| JP | 2008-253786 A | 10/2008 | | |
| WO | WO 9409392 A1 * | 4/1994 | | G02B 1/04 |

OTHER PUBLICATIONS

Office Action (Notification of Second Office Action) issued on Aug. 25, 2015, by the Patent Office of the People's Republic of China in corresponding Chinese Patent Application No. 201280042334.4, and an English Translation of the Office Action. (10 pages).
Canadian Office Action issued on Apr. 20, 2015, by the Canadian Patent Office in corresponding Canadian Patent Application No. 2,847,148. (2 pages).
Office Action (Text of the First Office Action) issued on Jan. 4, 2015, by the State Intellectual Property Office of the People's Republic of China in corresponding Chinese Patent Application No. 201280042334.4, and English translation of the Office Action. (10 pages).
Extended Search Report issued on Mar. 12, 2015, by the European Patent Office in corresponding European Patent Application No. 12835108.7-1455. (4 pages).
International Search Report (PCT/ISA/210) mailed on Dec. 25, 2012, by the Japanese Patent Office as the International Searching Authority for International Application No. PCT/JP2012/074419.
Notification of Third Office Action issued Apr. 6, 2016 by the Patent Office of the People's Republic of China in corresponding Chinese Patent Application No. 201280042334.4, and an English translation thereof (10 pages).
Notification of 4th Office Action issued Sep. 20, 2016 by the Patent Office of the People's Republic of China in corresponding Chinese Patent Application No. 201280042334.4, and an English translation thereof (13 pages).

* cited by examiner

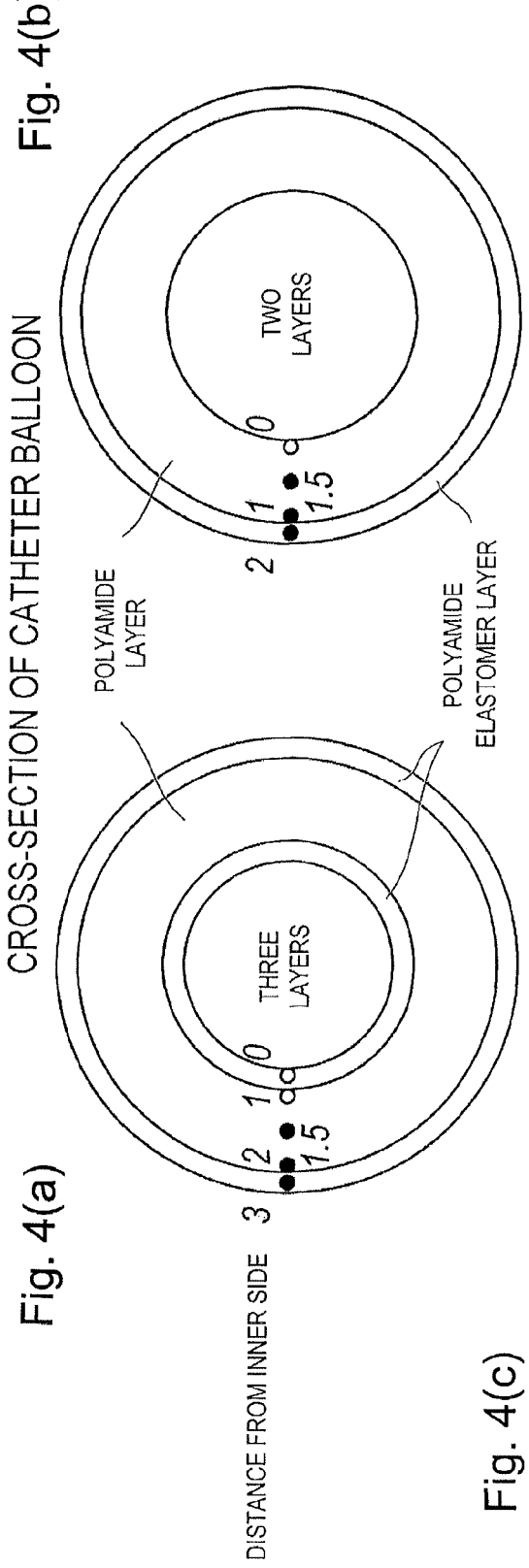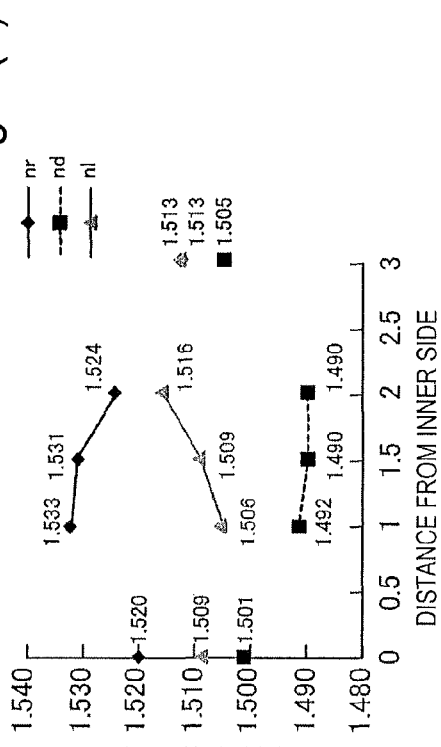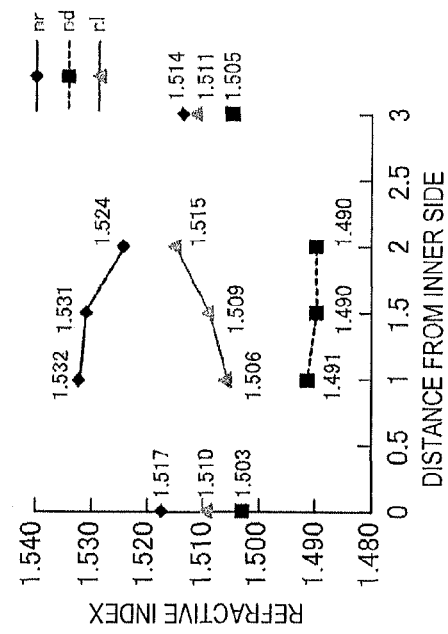

EXAMPLE 5

EXAMPLE 3

EXAMPLE 4

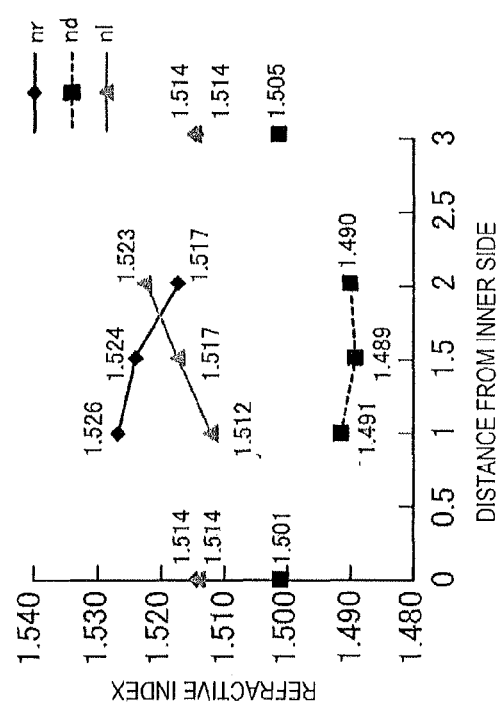
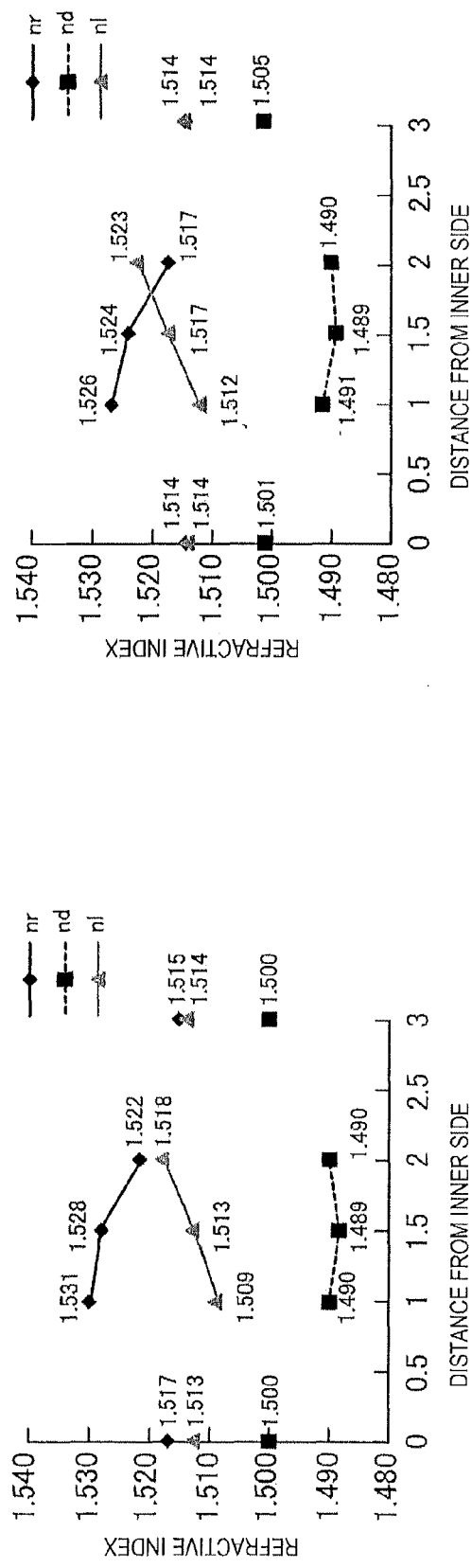

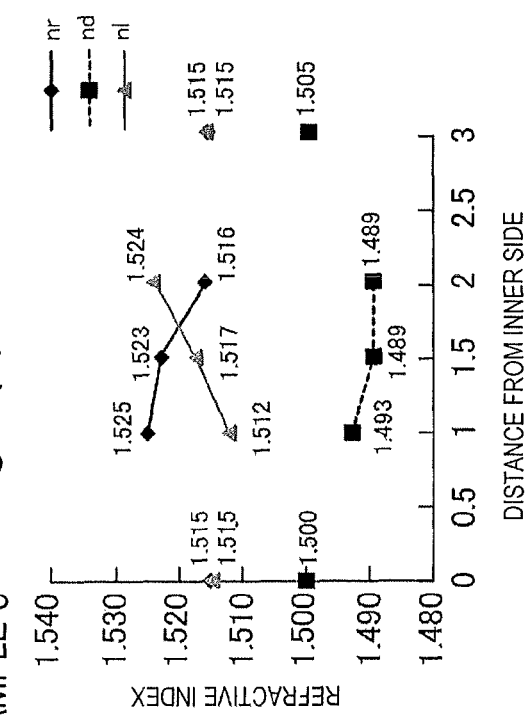
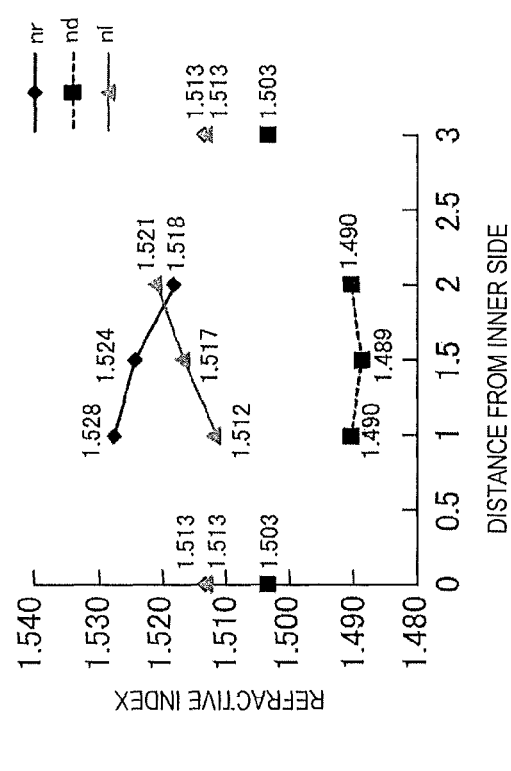

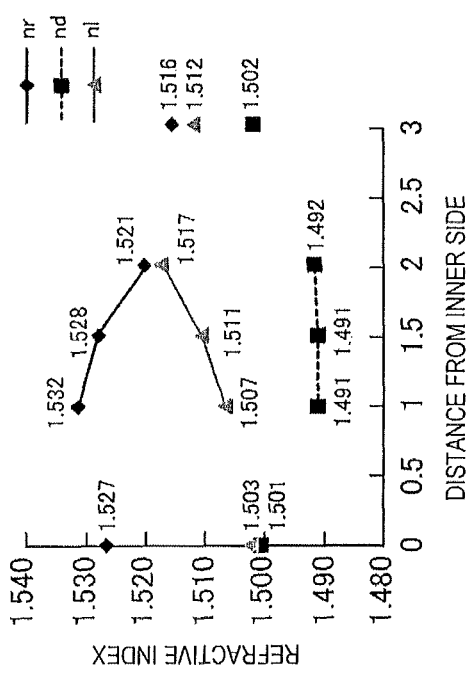
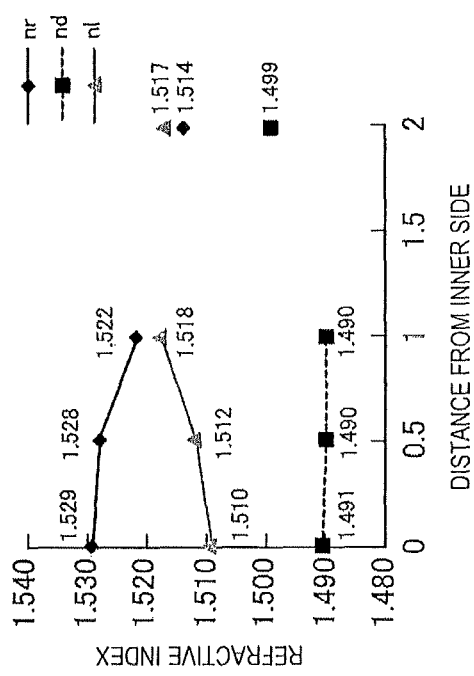
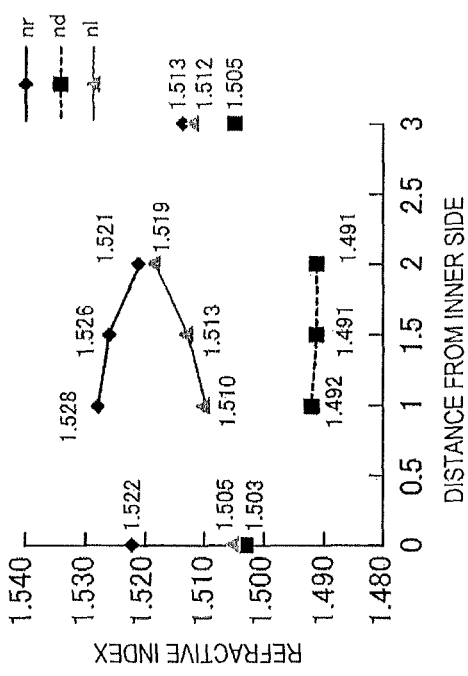
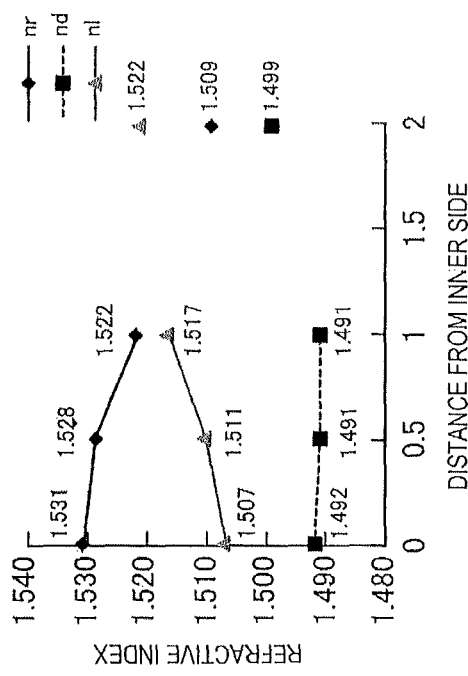

CATHETER BALLOON AND BALLOON CATHETER

CROSS REFERENCE TO RELATED APPLICATIONS

This application is a continuation of International Application No. PCT/JP2012/074419 filed on Sep. 24, 2012, and claims priority to Japanese Application No. 2011-214496 filed on Sep. 29, 2011, the entire content of both of which is incorporated herein by reference.

TECHNICAL FIELD

The present invention generally relates to a catheter balloon and a balloon catheter. More particularly, the present invention relates to a balloon and a balloon catheter configured to be inserted into a lumen in a living body.

BACKGROUND DISCUSSION

A catheter equipped with a balloon (balloon catheter) is used for body organ dilation, which is performed for maintaining a luminal space by placing a stent in a stenosed site of a lumen in the living body, such as a blood vessel, the bile duct, the esophagus, the trachea, the urethra, and other organs. Moreover, the catheter is also used for treating ischemic heart diseases or for urethral catheterization for patients having a difficulty in urination.

Accordingly, the balloon catheter is required to have properties including (1) trackability (a property that enables the balloon to move along the tortuous blood vessels and the like), (2) an ability to pass through stenosed sites of blood vessels and the like, (3) an ability to dilate stenosed sites of calcified blood vessels and the like, (4) compliance (an appropriate degree of non-extensibility by which the balloon catheter does not inflate any further once it has dilated up to a desired diameter), (5) a sufficient degree of strength and pressure resistance that enables the balloon catheter to endure the internal pressure or impact caused at the time of balloon dilation, and the like.

Particularly, the balloon portion is required to have compliance, pressure resistance, and flexibility and to be formed of a thin membrane. Materials previously used to fabricate catheter balloon satisfying such properties are polyethylene terephthalate, polyolefins, polyamide.

For example, a known balloon, which is obtained as disclosed in Japanese Application Publication No. 2008-253786 by selecting aliphatic-aromatic polyamide as a base polymer and making the aliphatic polyamide having a short carbon chain into a polymer alloy to improve compliance or pressure resistance, has aromatic rings in the main chain, and hence the pressure resistance and compliance thereof can be improved. However, this balloon is inferior to a balloon made of polyethylene terephthalate (PET) and the flexibility thereof is poorer than that of aliphatic polyamide.

For this reason, Japanese Application Publication No. 2008-253786 discloses a technique relating to a balloon obtained by adding inorganic crystals to the polymer.

Moreover, another technique of improving pressure resistance and flexibility is disclosed in Japanese Application Publication No. 2005-319289. This document discloses a technique of producing a balloon by biaxial stretch blow molding using a block polymer, which includes a polyamide-based hard segment and a glycol-based soft segment, as a material of the balloon membrane such that a calculated elastic modulus under a pressure caused at the time of balloon dilation becomes 1,300 MPa or higher.

SUMMARY

If inorganic crystals are added to the polymer as described in the Japanese Application Publication No. 2008-253786, pressure resistance or compliance of the balloon are definitely improved. However, the improvement in the flexibility or a property of thin membrane cannot be expected.

Moreover, the catheter balloon repeatedly dilates and contracts by medical practice. In the balloon which is disclosed in the Japanese Application Publication No. 2008-253786 and formed of a membrane that is merely a mixture of inorganic crystals and a polymer, the adhesion force between the polymer and the inorganic crystals is weak, and the inorganic crystals themselves do not easily dilate or contract. Consequently, when the balloon dilates, delamination occurs in the interface between the polymer and the inorganic crystal inside the membrane, and gaps are formed. These gaps act as cracks in the entire membrane as a mixture of the inorganic crystals and the polymer, hence rupture of the balloon membrane may start from the gaps.

Particularly, the balloon is generally in the form of a cylinder and has a structure that dilates due to the internal pressure thereof. Therefore, from a dynamic viewpoint, a maximum stress is applied to the innermost circumference thereof, and this leads to a problem that balloon membrane easily ruptures from the direction of the inner circumference if there are gap inside the membrane.

Furthermore, through the biaxial stretch blow molding that is performed as described in the Japanese Application Publication No. 2005-319289 by using the block copolymer, which includes a polyamide-based hard segment and a glycol-based soft segment, as a material of the balloon membrane, sufficient pressure resistance is not obtained.

Particularly, as described above, from a dynamic viewpoint, a maximum stress is applied to the innermost circumference of the balloon, hence the problem that the balloon membrane easily ruptures from the direction of the inner circumference thereof cannot be resolved.

The disclosure here is focused on the orientation of polymers in the catheter balloon membrane, and aims to provide a catheter balloon with improved pressure resistance of the entire membrane, and a balloon catheter including such catheter balloon, by converting the maximum stress applied to the innermost circumference into extensibility.

According to one aspect of the disclosure here, a cylindrical catheter balloon is formed of a membrane as a laminate of at least two or more layers including a polyamide elastomer layer and a polyamide layer. The polyamide elastomer layer is disposed at the inner side of the polyamide layer, a refractive index $n_{r1}$ in the circumferential direction of a cross-section perpendicular to the axis in the inner side the polyamide layer is greater than a refractive index $n_{r2}$ in the circumferential direction of a cross-section perpendicular to the axis in the inner side surface of the polyamide elastomer layer, and the difference between the refractive index $n_{r1}$ and the refractive index $n_{r2}$ is 0.01 or greater.

According to another aspect, a balloon catheter comprises an outer tube, an inner tube positioned in the outer tube, and a balloon possessing a proximal end portion fixed to the outer tube and a distal end portion fixed to the inner tube. The balloon is a membrane comprised of a laminate of at least two layers, with one of the layers being a polyamide elastomer layer and the other payer being a polyamide layer. The polyamide elastomer layer is disposed at the inner side of the polyamide layer, the refractive index $n_{r1}$ in a circumferential direction of a cross-section perpendicular to the axis in the inner side surface of the polyamide layer is greater than the refractive index $n_{r2}$ in the circumferential direction of a cross-section perpendicular to the axis in the inner side surface of the polyamide elastomer layer, and the difference between the refractive index $n_{r1}$ and the refractive index $n_{r2}$ is 0.01 or greater The foregoing, and additional features and characteristics of the catheter balloon and balloon catheter disclosed here, will become more apparent from the following detailed description considered with reference to the accompanying drawing figures in which like element are designated by like reference numerals.

BRIEF DESCRIPTION OF DRAWINGS

FIGS. 4(a) and 4(b) are schematic views of catheter balloon examples, and FIGS. 4c and 4d show experimental data associated with the catheter disclosed here.

FIGS. 6(a) and 6(b) shows experimental data of examples of the catheter disclosed here.

FIGS. 7(a) and 7(b) show experimental data of examples of the catheter disclosed here.

FIGS. 8(a), 8(b), 8(c) and 8(d) show experimental data of comparative examples of a catheter.

DETAILED DESCRIPTION

A first aspect of the disclosure here involves a cylindrical catheter balloon formed of a membrane, wherein the membrane is in the form of a laminate of at least two or more layers including a polyamide elastomer layer and a polyamide layer, in which the polyamide elastomer layer is disposed at the inner side of the polyamide layer, a refractive index $n_{r1}$ in the circumferential direction of a cross-section perpendicular to the axis in the surface of inner side of the polyamide layer is greater than a refractive index $n_{r2}$ in the circumferential direction of a cross-section perpendicular to the axis in the surface of inner side of the polyamide elastomer layer, and a difference between the refractive index $n_{r1}$ and the refractive index $n_{r2}$ is 0.01 or greater.

A catheter balloon constructed as briefly described above exhibits improvements in terms of pressure resistance compared to conventional catheter balloons.

Moreover, it is possible to inhibit the balloon portion from dilating due to pressurization while maintaining a similar flexibility and pass-through ability that the conventional balloon has. Furthermore, it is possible to reliably dilate a lesion and avoid damaging the mucous membrane or the inner lining of blood vessels.

Accordingly, if the balloon disclosed here is used, it is possible to obtain a balloon catheter which exhibits excellent trackability at the time of the balloon dilation, inhibits cracking or crazing as a starting point of rupture, and has excellent mechanical strength and flexibility.

In addition, the compliance of the balloon of the balloon disclosed here, which represents how easily the balloon diameter can be increased, is as low as 0.012 mm/atm or less. Therefore, it is possible to rather dramatically inhibit the balloon portion from stretching due to the pressurization, while maintaining flexibility and pass-through ability similar to that which a conventional balloon exhibits.

The structure of the catheter balloon disclosed here will be described first with reference to the drawings, and then the properties and each constituent of the balloon will be described below. It is to be understood that FIGS. 1A and 1B merely illustrate examples of the catheter balloon disclosed here, and the scope of the invention is not limited to these illustrated versions of the balloon.

Figure 1A:
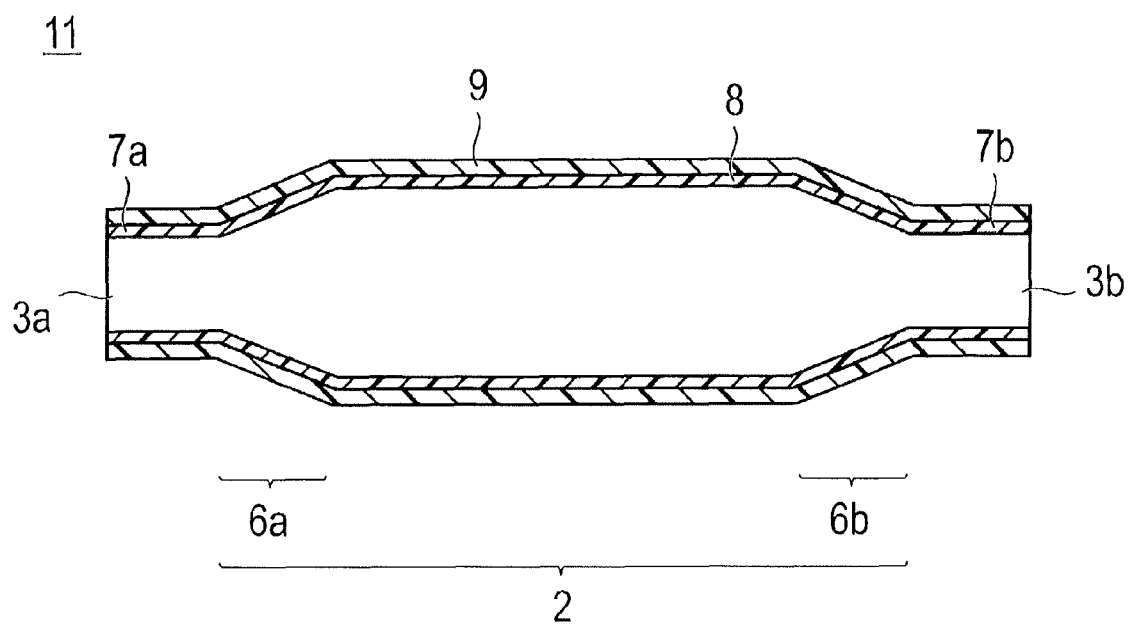
FIG. 1A is a longitudinal cross-sectional view of a catheter representing one example of the catheter disclosed here.
Figure 1B:
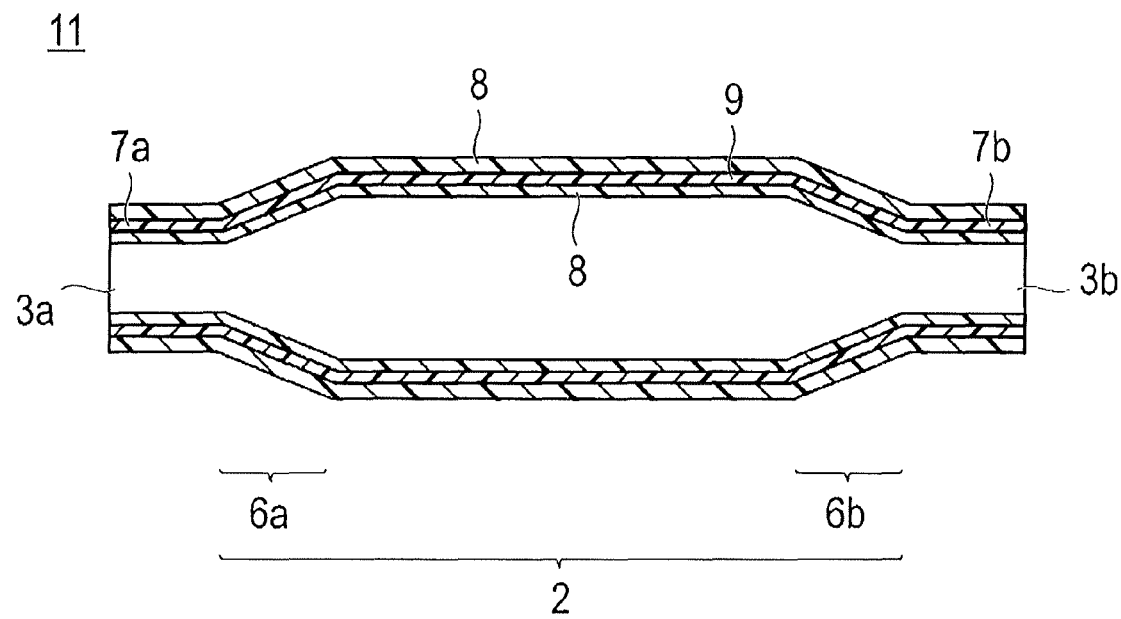
FIG. 1B is a longitudinal cross-sectional view of a catheter representing another example of the catheter disclosed here.

FIG. 1A illustrates, in longitudinal cross-section, an embodiment of the catheter balloon representing one example of the catheter balloon disclosed here. In the embodiment shown in FIG. 1A, the balloon has a two-layer structure consisting of a polyamide layer and a polyamide elastomer layer. FIG. 1B illustrates, in longitudinal cross-section, an embodiment of the catheter balloon representing another example of the catheter balloon disclosed here. In the FIG. 1B version, the balloon has a three-layer structure in which a polyamide elastomer layer 8, a polyamide layer 9, and the polyamide elastomer layer 8 are laminated on each other in this order.

It is preferable for a catheter balloon 11 to be configured as a cylindrical membranous body 2 that can dilate or contract by fluid supplied from a catheter. It is also preferable for the catheter balloon 11 to be configured to include connection portions 7a and 7b that extend from both ends in the axial direction of the membranous body and that are connected to the catheter.

In the respective connection portions 7a and 7b at both ends, opening portions 3a and 3b through which a catheter is inserted or passes are formed.

It is preferable for the opening portion 3b of one of the connection portions to have an inner diameter larger than that of the opening portion 3a of the other connection portion.

Moreover, the catheter balloon 11 has a cylindrical portion which is for dilating stenosed portions of lumens in the body, such as blood vessels, the ureter, and the bile duct, and has a practically uniform outer diameter.

As shown in FIGS. 1A and 1B, both ends of the cylindrical membranous body 2 may have a tapered shape (portion with a gradient).

That is, it is preferable for the balloon to have the cylindrical membranous body 2 including tapered portions 6a and 6b that have the shape of a (approximately) truncated cone (or the shape of an approximately truncated pyramid), becoming narrower toward both ends, and the connection portions 7a and 7b that are linked (directly linked) respectively to the tapered portions 6a and 6b and are connected to the catheter extend out of the axial direction.

Further, in the connection portions 7a and 7b at both ends, the opening portions 3a and 3b through which the catheter is inserted are respectively formed.

When both ends of the cylindrical membranous body have a tapered shape, the portion where the diameter of the balloon is maximized continues in the central portion of the cylindrical membranous body. Moreover, the tapered portions 6a and 6b continue from the central portion of the cylindrical membranous body and show the change in which the diameter continuously decreases toward the ends.

The connection portions 7a and 7b connected to the catheter continue respectively from the tapered portions 6a and 6b, and both connection portions 7a and 7b possesses outer diameters of the same size that continue along the length of the connection portions 7a and 7b and inner diameters of the same that continue along the length of the connection portions 7a and 7b. A balloon is mounted on the catheter in the connection potions 7a and 7b, and the opening portions 3a and 3b are formed respectively in these portions.

In addition, the tapered portions 6a and 6b and the connection portions 7a and 7b connected with the catheter are respectively positioned in both ends of the cylindrical membranous body of the balloon. The shapes of the respective tapered portions and connections portions may be different from each other.

The catheter balloon is formed of a membrane having a multi-layer structure as a laminate of at least two or more layers including a polyamide elastomer layer and a polyamide layer. The catheter balloon is preferably formed of a membrane having one to three polyamide elastomer layers and one to two polyamide layers, and more preferably formed of a membrane having two polyamide elastomer layers and one polyamide layer.

If the polyamide elastomer is laminated on the polyamide as described above, a parison, which will be described later, can be rather easily molded by coextrusion. Moreover, flexibility and pass-through ability required for a catheter balloon as well as pressure resistance can be established simultaneously.

Regarding the order of laminating the polyamide elastomer layer 8 and the polyamide layer 9, as long as a laminate structure, in which the polyamide elastomer layer 8 is disposed at the innermost side and the polyamide layer 9 is laminated on the outer surface of the polyamide elastomer layer 8, is established, other layers may be laminated in any order without particular limitation.

It is particularly preferable for the catheter balloon to be configured to include a membrane having a three-layer structure in which the polyamide elastomer layer 8, the polyamide layer 9, and the polyamide elastomer layer 8 are laminated on each other in this order.

If the polyamide elastomer layer is formed as an outermost layer, the balloon exhibits flexibility when inserted into the body by being mounted on a catheter. Accordingly, the balloon excellently passes through lumens in the body, such as blood vessels.

Moreover, the surface of the polyamide elastomer layer provided as an outermost layer or the polyamide layer may be optionally coated with a biocompatible material or an antithrombotic material.

As the biocompatible material or the antithrombotic material, one kind among various known polymers may be used alone, or a mixture of such various known polymers may be used. For example, natural polymers (collagen, gelatin, chitin, chitosan, cellulose, polyaspartic acid, polyglutamic acid, polylysine, casein, and the like), synthetic polymers (phosphatide polymers and Methacryloyloxyethyl Phosphorylcholin (MPC) block polymers having a phosphoric acid group on the side chain thereof), polyhydroxyethyl methacrylate, hydroxyethyl methacrylate-styrene copolymers (for example, a HEMA-St-HEMA block copolymer), polymethyl methacrylate, polylactic acid, polyglycolic acid, a lactic acid-glycolic acid copolymer, polyethylene, polypropylene, and the like can be preferably used.

In order to make it relatively easy to insert the catheter balloon into blood vessels or a guide catheter, it is preferable to treat the outer surface of the balloon or the membranous body such that the outer surface of the balloon or the membranous body exhibits lubricity when coming into contact with blood and the like.

Examples of the above treatment include a method of coating the surface with hydrophilic polymers such as poly(2-hydroxyethylmethacrylate), polyhydroxyethyl acrylate, hydroxypropyl cellulose, methyl vinyl ether-maleic anhydride copolymers, polyethylene glycol, polyacrylamide, polyvinyl pyrrolidone, and random or block copolymers of dimethylacrylamide-glycidyl methacrylate, a method fixing these polymers onto the surface, and the like.

It is preferable for the polyamide elastomer layer to be formed while being in close contact with the surface of the polyamide layer. Furthermore, it is preferable for the polyamide elastomer layer to be formed while being in close contact with the entire surface of the polyamide layer.

In this manner, a catheter balloon with improved pressure resistance can be provided.

As described above, the catheter balloon disclosed by way of example here is a cylindrical membranous body in which a polyamide elastomer layer is disposed at the inner side of a polyamide layer, in which a refractive index $n_{r1}$ in the circumferential direction of a cross-section perpendicular to the catheter balloon axis in the inner side surface of the polyamide layer is greater than a refractive index $n_{r2}$ in the circumferential direction of a cross-section perpendicular to the catheter balloon axis in the inner side surface of the polyamide elastomer layer, and a difference between the refractive index $n_{r1}$ and the refractive index $n_{r2}$ is 0.01 or greater (i.e., the refractive index difference is at least 0.01).

The difference between the refractive index $n_{r1}$ in the circumferential direction of a cross-section perpendicular to the axis in the inner side surface of the polyamide layer and the refractive index $n_{r2}$ in the circumferential direction of a cross-section perpendicular to the axis in the inner side surface of the polyamide elastomer layer is preferably from 0.01 to 0.02 and more preferably from 0.01 to 0.015.

As described above, if the polyamide elastomer layer is disposed at the inner side of the polyamide layer, and the difference between the refractive index $n_{r1}$ in the circumferential direction of a cross-section perpendicular to the axis in the inner side surface of the polyamide layer and the refractive index $n_{r2}$ in the circumferential direction of a cross-section perpendicular to the axis in the inner side surface of the polyamide elastomer layer is 0.01 or greater, the number of the polyamide elastomer molecules in the polyamide elastomer layer that are oriented in the circumferential direction becomes relatively small. Consequently, the polyamide elastomer layer obtains a margin for stretching.

It is considered that for this reason, the stress applied to the innermost circumference can be converted into extensibility of the polyamide elastomer layer.

Described in more detail, it is known that in the system in which internal pressure is applied to a cylindrical substance or member such as a catheter balloon, theoretically, a maximum stress is applied to the innermost circumference of the cross-section perpendicular to the axis of the cylindrical substance, and the stress decreases toward the radial direction of the cross-section perpendicular to the axis (cylinder model). Actually, it has been confirmed that when internal pressure is applied to the catheter balloon, rupture of the balloon starts from the side of the innermost circumference in many cases.

With the catheter balloon disclosed here, a flexible polyamide elastomer layer, in which a relatively small number of polymers are oriented in the circumferential direction, is disposed at the side of the innermost circumference (innermost circumferential side) to which a maximum stress is applied, whereby the maximum stress applied to the innermost circumference is converted into extensibility of the flexible polyamide elastomer layer. It is considered that for this reason, the internal pressure applied to the balloon can be effectively absorbed in the system of the catheter balloon.

On the other hand, since a hard polyamide layer, in which the number of polymers oriented in the circumferential direction is relatively larger than that of the flexible polyamide elastomer layer, is disposed at the outside of the polyamide elastomer layer, the strength of the entire catheter balloon can be maintained.

Moreover, in the balloon membrane disclosed here, a large number of polymer chains are crystallized in the hard polyamide layer in which a relatively large number of polymers are oriented in the circumferential direction. Accordingly, an effect that results in excellent compliance is also obtained.

From the above facts, by controlling the orientation state of polymer chains in each layer of the membrane as a laminate of at least two layers including a polyamide layer and a polyamide elastomer layer constituting the catheter balloon, the pressure resistance that makes the rupture starting from the inner side occur less compared to the conventional catheter balloon is improved.

The orientation state of the polymer chains can be confirmed by measuring birefringence in general.

For example, in a uniaxially stretched polymer film, the molecular chains are oriented in the stretch direction. Accordingly, there is a difference between a refractive index in the stretch direction and a refractive index in a direction perpendicular to the stretch direction. This results in anisotropy of the refractive index of light, and can be measured as birefringence.

Methods of measuring birefringence mentioned above include (1) an intensity method, (2) a compensation method, (3) observation of polarization color, and the like.

According to examples disclosed here, birefringence is measured by the (2) compensation method as follows, and then a refractive index ($n_r$) in the circumferential direction of a cross-section perpendicular to the axis of the balloon, a refractive index ($n_l$) in the long axis direction of the balloon, and a refractive index ($n_d$) in a radial direction of the cross-section perpendicular to the axis of the balloon are calculated.

A relative refractive index used in here is calculated by three-dimensional analysis using a polarization microscope.

The cross-section of a fragment having a thickness of 16 μm that is sliced from the central portion of the straight tube portion of the balloon and the cross-section of a fragment that is sliced in the long axis direction were observed with a polarization microscope, and retardation thereof was measured using a compensator to calculate a birefringence Δn of the cross-section and a birefringence Δn of the long axis by the following Formulae (1) to (3).

$$\Delta n = R \div t \quad \text{Formula (1)}$$

$$R = C \times f(i) \quad \text{Formula (2)}$$

$$f(i) = \sin^2 i (1 + 0.2041 \times \sin^2 i + 0.0627 \times \sin^4 i) \quad \text{Formula (3)}$$

(In the Formulae (1) to (3), R indicates retardation (nm), t indicates the thickness (16 (μm)) of a sample, C indicates a constant of $0.822 \times 10^4$ that depends on the thickness of a crystal mounted on the compensator, and i indicates a correction angle (Radian) of the compensator.)

Subsequently, the birefringence Δn of the cross-section and the birefringence Δn of the long axis calculated by the Formulae (1) to (3) are assigned to the following Equations (1) to (3) to calculate solutions of a refractive index ($n_r$) in the circumferential direction of the cross-section perpendicular to the axis, a refractive index ($n_L$) in the long-axis direction, and a refractive index ($n_d$) in the radial direction (thickness direction) of the cross-section perpendicular to the axis respectively.

$$\Delta n(\text{Cross-section}) = |n_r - n_d| \quad \text{Equation (1)}$$

$$\Delta n(\text{Long axis}) = |n_L - n_d| \quad \text{Equation (2)}$$

$$n^2 = (n_r^2 + n_L^2 + n_d^2) \div 3 \quad \text{Equation (3)}$$

Solution:

$$n_r = \left(-b + \sqrt{b^2 - 12c}\right) \div 6$$

$$n_L = n_D + \Delta n(\text{Long axis})$$

$$n_d = n_r - \Delta n(\text{Cross-section})$$

$$b = 2\Delta n(\text{Long axis}) - 4\Delta n(\text{Cross-section})$$

$$c = 2(\Delta n(\text{Cross-section}))^2 + (\Delta n(\text{Long axis}))^2 - 2\Delta n(\text{Cross-section}) \times \Delta n(\text{Long axis}) - 3n^2$$

(In the Equations (1) to (3) and solutions, Δn (cross-section) indicates a birefringence in the slicing direction, Δn (long axis) indicates a birefringence in the long-axis direction, $n_r$ indicates a refractive index in the circumferential direction, $n_L$ indicates a refractive index in the long-axis direction, $n_d$ indicates a refractive index in the thickness direction, and n is 1.51 (average refractive index.))

In this manner, as described in the experimental results which will be shown later in examples, it is possible to calculate the refractive index ($n_r$) in the circumferential direction of the cross-section perpendicular to the axis, the refractive index ($n_L$) in the long-axis direction, and the refractive index ($n_d$) in the radial direction of the cross-section perpendicular to the axis in any position in each layer of the catheter balloon having the multi-layer structure, by means of the above measurement method using a polarization microscope.

Moreover, by calculating the refractive index ($n_r$) in the circumferential direction of the cross-section perpendicular to the axis, the refractive index ($n_L$) in the long-axis direction, and the refractive index ($n_d$) in the radial direction of the cross-section perpendicular to the axis by the above method, the orientation state of polymer chains in each direction can be specified.

For example, the larger the value of $n_r$ is, the more the polymer chains are likely to be oriented in the circumferential direction, and the larger the value of $n_L$ is, the more the polymer chains are likely to be oriented in the long-axis direction. Furthermore, the smaller the value of $n_d$ is, the more the polymer chains are likely to exhibit plane orientation, and if $n_r$ and $n_L$ have the same value, the polymer chains may be oriented in an isotropic state.

In the catheter balloon here, $n_{r2}$ of the polyamide elastomer layer is smaller than $n_{r1}$ of the polyamide layer by 0.01 or a larger value. Accordingly, in the polyamide elastomer layer, the degree of orientation in the circumferential direction is relatively low, hence the innermost circumference of the balloon obtains a margin for stretching.

In the present specification, regarding each of the refractive indices of the surface of inner side of the polyamide elastomer layer that is disposed at the innermost side of the balloon, a refractive index in the circumferential direction of the cross-section perpendicular to the axis is denoted as $n_{r2}$, a refractive index in the long-axis direction is denoted as $n_{L2}$, and a refractive index in the radial direction of the cross-section perpendicular to the axis is denoted as $n_{d2}$. Moreover, regarding each of the refractive indices of the surface of inner side of the polyamide layer that is laminated on the surface of the polyamide elastomer layer, a refractive index in the circumferential direction of the cross-section perpendicular to the axis is denoted as $n_{r1}$, a refractive index in the long-axis direction is denoted as $n_{L1}$, and a refractive index in the radial direction of the cross-section perpendicular to the axis is denoted as $n_{d1}$.

Herein, each of the refractive indices of the inner side surface of the polyamide layer refers to a refractive index in the area of the polyamide layer near the inner surface (interface between the polyamide layer and the polyamide elastomer layer) of the polyamide layer. For example, the refractive index in the circumferential direction of the cross-section perpendicular to the axis of the inner side surface of the polyamide layer refers to a refractive index in the circumferential direction that is found in an area which starts from the inner surface of the polyamide layer and is equal to or smaller than one third of the thickness of the entire polyamide layer.

Furthermore, herein, each of the refractive indices of the inner side surface of the polyamide elastomer layer refers to a refractive index in the area of the polyamide elastomer layer near the inner surface of the polyamide elastomer layer. For example, the refractive index in the circumferential direction of the cross-section perpendicular to the axis of the inner side surface of the polyamide elastomer layer refers to a refractive index in the circumferential direction that is found in an area which starts from the inner surface of the polyamide elastomer layer and is equal to smaller than one-half the thickness of the entire polyamide elastomer layer.

Regarding the size of the catheter balloon disclosed here, the outer diameter of the cylindrical membranous body is preferably 1 mm to 35 mm and preferably 1.5 mm to 30 mm when the balloon dilates. Moreover, the length of the cylindrical membranous body in the long-axis direction is 3 mm to 80 mm and preferably 10 mm to 75 mm, and the full length of the balloon (total length of the cylindrical membranous body and the connection portions in the long-axis direction) is 5 mm to 120 mm and preferably 15 mm to 100 mm.

The shape of the cross-section perpendicular to the axis of the balloon is not particularly limited and may be a circle, an ellipse, an approximately elliptical shape, an approximately circular shape, or a polygonal columnar shape. It is preferable for the balloon disclosed here to have a cylindrical shape.

When the catheter balloon disclosed here contracts, the average thickness (thickness) thereof is preferably 5 µm to 50 µm and more preferably 10 µm to 30 µm.

If the average thickness of the catheter balloon is within a range of 5 µm to 50 µm at the time of contraction, this is preferable in view of trackability or the ability to pass through stenosed portions of blood vessels and the like.

The connection portions of the catheter balloon here may be integrated (monolithically molded) with the membranous body 2 as described in FIG. 1A or 1B shown above, or may be separately bonded to the membranous body, in the form of a membranous substance which has a diameter smaller than that of the membranous body 2 and an approximately cylindrical shape.

In a normal state, the average thickness of the connection portions in the catheter balloon disclosed here is preferably 5 µm to 50 µm, more preferably 10 µm to 30 µm.

The catheter balloon includes a membranous body that can dilate or contract by fluid supplied from a catheter. Therefore, the catheter balloon is foldable and can contract in a state of being folded around the outer circumference of the body of the catheter.

The average thickness of the polyamide layer constituting the catheter balloon here is preferably 0.5 µm to 49.5 µm, more preferably 5 µm to 25 µm.

This is because flexibility and pass-through ability required for a catheter balloon as well as pressure resistance can be established simultaneously.

The polyamide layer forming a part of the catheter balloon disclosed here contains polyamide in an amount of 50% by weight to 100% by weight, and so pressure resistance or compliance required for a catheter balloon is secured.

The polyamide that can be preferably used for the polyamide layer in the catheter balloon disclosed here is not particularly limited as long as it has an acid amide bond (—CO—NH—) on a main chain, and is produced by polymerization (homopolymerization) of lactam or amino acid having a cyclic structure or condensation polymerization of dicarboxylic acid and diamine in general.

Therefore, it is preferable to use homopolyamide as the polyamide.

Examples of homopolymerizable monomers include ε-caprolactam, aminocaproic acid, enantholactam, 7-aminoheptanoic acid, 11-aminoundecanoic acid, 12-aminododecanoic acid, 9-aminononanoic acid, peperidone, and the like.

Examples of the dicarboxylic acid to be subjected to condensation polymerization together with diamine include adipic acid, sebacic acid, dodecanedicarboxylic acid, glutaric acid, terephtalic acid, 2-methylterephthalic acid, isophthalic acid, naphthalene dicarboxylic acid, and the like.

Examples of the diamine include tetramethylenediamine, hexamethylenediamine, nonamethylenediamine, decamethylenediamine, undecamethylenediamine, dodecamethylenediamine, paraphenylenediamine, metaphenylenediamine, and the like.

As the polyamide, those having other segments such as polyester and polyether are preferable. The polyamide may be used in the form of a commercially available product or may be synthesized. Examples of commercially available polyamide include nylon 4, 6, 7, 8, 11, 12, 6.6, 6.9, 6.10, 6.11, 6.12, 6T, 6/6.6, 6/12, 6/6T, 6T/6I, and the like.

Moreover, the terminal of the polyamide may be sealed with a carboxyl group, an amino group, or the like.

One kind of polyamide resin may be used alone, or two or more kinds of polyamide resin may be used in combination.

Among the above, nylon 11 and nylon 12 are particularly preferable as the polyamide used in the catheter balloon here.

The weight average molecular weight of the polyamide used in the catheter balloon here is preferably 10,000 to 500,000, more preferably 15,000 to 400,000, and even more preferably 20,000 to 300,000.

If the molecular weight of the polyamide used for the polyamide layer is 10,000 to 500,000, mechanical strength sufficient for improving pressure resistance is obtained.

The weight average molecular weight of the polyamide can be measured by known methods such as MS spectrometry, a light scattering method, liquid chromatography, and gas chromatography. In the present specification, a molecular weight measured by gel permeation chromatography is used.

The measurement conditions are as follows. Mobile phase: hexafluoroisopropanol (including 5 mmol/L of additive $CF_3COONa$); standard substance: standard PMMA/dimethyl terephthalate; injection amount: 100 μL; a flow rate: 1 mL/min, column temperature: 40° C., concentration: 0.1 w/v % DS-4; column: Shodex GPC HFIP-806M-2+HFIP-803, detector: Shodex RI-71

Regarding each of the refractive indices in the inner side surface of the polyamide layer (interface between the polyamide layer and the polyamide elastomer layer) disclosed here, the refractive index ($n_{r1}$) in the circumferential direction of the cross-section perpendicular to the axis is preferably 1.520 to 1.540, the refractive index ($n_{L1}$) of the long-axis direction is preferably 1.500 to 1.520, and the refractive index ($n_{d1}$) in the radial direction of the cross-section perpendicular to the axis is preferably 1.480 to 1.510. The refractive index ($n_{r1}$) in the circumferential direction of the cross-section perpendicular to the axis is more preferably 1.525 to 1.535, the refractive index ($n_{L1}$) in the long-axis direction is more preferably 1.505 to 1.515, and the refractive index ($n_{d1}$) in the radial direction of the cross-section perpendicular to the axis is more preferably 1.485 to 1.500.

Each of the refractive indices of the surface of inner side of the polyamide layer (inner circumferential surface of the polyamide layer) is obtained by the compensation method and calculation method described above.

Needless to say, the above refractive index may be different from each of refractive indices obtained by other methods in some cases.

Examples of the additives that are optionally added to the polyamide layer include higher alcohols, hydroxybenzoic acid ester, aromatic sulfonamide, and the like, but the catheter balloon disclosed here is not limited to these.

Furthermore, the radiopaque substances that are optionally added to the polyamide layer are not particularly limited as long as they do not transmit X rays, and known radiopaque substances can be used.

Specific examples of such radiopaque substances include iodine, barium, bismuth, boron, bromine, calcium, gold, platinum, silver, iron, manganese, nickel, gadolinium, dysprosium, tungsten, tantalum, stainless steel, nitinol, barium sulfate, compounds of these, and solution/dispersion (for example, a physiological salt solution); amidotrizoic acid (3,5-diacetamino-2,4,6-triiodobenzoic acid), meglumine sodium amidotrizoate, meglumine amidotrizoate, sodium iothalamate, meglumine iothalamate, meglumine iotroxate, iotrolan, ioxaglic acid, ioxalan, iopamidol, iopromide, iohexyl, ioversol, iomeprol; fatty acid ethyl esters of iodized poppy oil (for example, Lipiodol™ as poppy seed oil having iodized carbon atoms); and the like.

One kind of the radiopaque substance may be used alone, or two or more kinds of radiopaque substances may be used in the form of a mixture.

Alternatively, a contrast layer containing the above substance as a base may be further laminated on the membranous body.

In this manner, how the balloon has dilated can be confirmed by radioscopy, and accordingly, the position of the balloon can be relatively clearly and easily confirmed.

The polyamide elastomer layer used in the catheter balloon here contains a polyamide elastomer. The polyamide elastomer layer may optionally contain known additives or radiopaque substances or may be constituted only with at least one or more kinds of polyamide elastomers.

Therefore, one kind of polyamide elastomer may be used alone, or two or more kinds of polyamide elastomer may be used in combination.

The polyamide elastomer layer forming part of the catheter balloon here contains the polyamide elastomer in an amount of 50% by weight to 100% by weight, and so the trackability required for a catheter balloon, an ability to pass through stenosed portions of blood vessels and the like, and the flexibility necessary for an ability to dilate stenosed portions of calcified blood vessels and the like are obtained.

The average thickness of the polyamide elastomer layer constituting the catheter balloon here is preferably 0.5 μm to 10 μm, more preferably 1 μm to 5 μm.

If the average thickness is 0.5 μm to 10 μm, flexibility and pass-through ability required for a catheter balloon as well as pressure resistance can be established simultaneously.

The polyamide elastomer that is preferably used for the polyamide elastomer layer here is preferably a polyamide block copolymer and more preferably a diblock copolymer consisting of a hard segment and a soft segment.

Examples of the diblock copolymer include polyamide (hard segment)-polyether (soft segment) block copolymers, which specifically include a nylon 11-polytetramethylene glycol block copolymer and a nylon 12-polytetramethylene glycol block copolymer.

The content of the soft segment in the polyamide elastomer is preferably 1 wt % to 50 wt %, more preferably 10 wt % to 30 wt %.

The shore D hardness of the polyamide elastomer is preferably 50 to 80, more preferably 55 to 63.

The tensile modulus of the polyamide elastomer is preferably 200 MPa to 600 MPa, more preferably 230 MPa to 500 MPa.

It is preferable for the polyamide elastomer to have a block copolymer represented by the following Chemical formula (1) or (2) on the polymer chain.

Chemical formula (1)

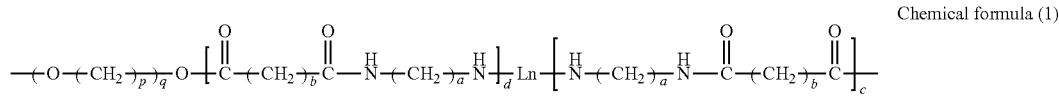

(In the Chemical formula (1), a is an integer of 4 to 12, b is an integer of 4 to 10, c is an integer of 0 to 100, d is an integer of 0 to 100, p is an integer of 2 to 4, q is an integer of 1 to 100, Ln is a linker site which is —C(O)—R—O—

C(O)—, and R is an alkylene group having 2 to 12 methylene groups.)

Chemical formula (2)

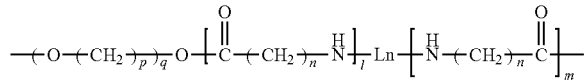

(In the Chemical formula (2), n is an integer of 5 to 11, l is an integer of 0 to 100, m is an integer of 0 to 100, p is an integer of 2 to 4, q is an integer of 1 to 100, Ln is a linker site which is —C(O)—R—O—C(O)—, and R is an alkylene group having 2 to 12 methylene groups.)

That is, the polyamide elastomer disclosed by way of example here may be the polyamide block copolymer itself represented by the Chemical formula (1) or (2) or a substance which is obtained by further polymerizing the polyamide block copolymer represented by the Chemical formula (1) or (2) by means of melt polymerization. However, the polyamide elastomer is preferably a substance which is obtained by further polymerizing the polyamide block copolymer represented by the Chemical formula (1) or (2) by means of melt polymerization.

Accordingly, when the polyamide elastomer is further polymerized by melt polymerization, the polyamide block copolymer represented by the Chemical formula (1) or (2) becomes, so to speak, a "repeating unit".

Moreover, R in the Chemical formulae (1) and (2) is not particularly limited and may be linear, branched, or cyclic, as long as R is an alkylene group having 2 to 12 methylene groups. Specific examples thereof include a tetramethylene group, a 2-methylpropyl group, a 1,1-dimethylethylene group, an n-pentylene group, an n-hexylene group, an n-nonylene group, a 1-methyloctylene group, a 6-methyloctylene group, a 1-ethylheptylene group, a 1-(n-butyl)pentylene group, a 4-methyl-1-(n-propyl)pentylene group, a 1,5,5-trimethylhexylene group, a 1,1,5-trimethylhexylene group, an n-decylene group, a 1-methylnonylene group, a 1-ethyloctylene group, a 1-(n-butyl)hexylene group, a 1,1-dimethyloctylene group, a 3,7-dimethyloctylene group, an n-undecylene group, a 1-methyldecylene group, and the like.

The polyamide elastomer that is further polymerized as described above can be obtained by performing melt polymerization on the polyamide elastomer of which both terminals are not sealed.

The melt polymerization can be performed by conducting heating for a certain time (12 to 96 hours) under vacuum by using a vacuum drier (VOS301 SD manufactured by Tokyo Rikakikai Co., Ltd.) having a cooling function (cooling machine; UT-4000L manufactured by Tokyo Rikakikai Co., Ltd.) and a vacuum pump (GCD136XN manufactured by ULVAC KIKO, Inc.).

When the polyamide block copolymer represented by the Chemical formula (1) or (2) is used for the polyamide elastomer layer according to the present invention, one kind of the polyamide block copolymer represented by the Chemical formula (1) or (2) may be used alone, or two or more kinds thereof may be used in combination.

The weight average molecular weight of the polyamide elastomer is preferably 10,000 to 500,000, more preferably 15,000 to 400,000, and even more preferably 20,000 to 300,000.

Moreover, the molecular weight of the polyamide elastomer is measured by the same method as the method used for polyamide.

If the weight average molecular weight of the polyamide elastomer is 10,000 to 500,000, extensional viscosity increases, and stretching caused by pressurization is suppressed. Accordingly, a degree of the overall compliance of the balloon decreases.

The polyamide elastomer used in the catheter balloon here may be synthesized, or a commercially available product may be purchased as the polyamide elastomer. Examples of the polyamide elastomer usable in the present invention include ELG5660 (manufactured by EMS-GRIVORY, trade name; Grilflex), ELG6260 (manufactured by EMS-GRIVORY, trade name; Grilflex), a high-molecular weight substance (having a melt viscosity of 1,260 Pa·s to 3,489 Pa·s) obtained by performing melt polymerization on the ELG5660, a high-molecular weight substance (having a melt viscosity of 5,282 Pa·s to 7,391 Pa·s) obtained by performing melt polymerization on the ELG6260, and the like.

Furthermore, the terminal of the polyamide elastomer may be sealed with a carboxyl group, an amino group, and the like.

The melt viscosity of the polyamide elastomer is preferably 500 Pa·s or higher and more preferably 500 Pa·s to 20,000 Pa·s.

This is because stretching caused by pressurization is suppressed, and a degree of the overall compliance of the balloon decreases.

In the discussion below, the melt viscosity is measured using a flow tester "CFT-500D manufactured by Shimadzu Corporation".

The additives or radiopaque substances that the polyamide elastomer layer may optionally contain are the same as those that the polyamide layer may contain. Accordingly, a detailed description of such additives or radiopaque substances will not be repeated.

In a particularly preferable embodiment of the material of the catheter balloon disclosed here, the weight average molecular weight of the polyamide is 20,000 to 50,000, and the weight average molecular weight of the polyamide elastomer is 20,000 to 500,000. Moreover, if nylon 12 is selected as the polyamide, and a nylon 12-polytetramethylene glycol block copolymer is selected as the polyamide elastomer, the difference in the refractive index can be rather easily controlled to be 0.01 or greater.

Set forth next is a description of a preferred, though non-limiting, production method for producing the catheter balloon disclosed here.

It is preferable for the production method for the catheter balloon to include a step 1 in which a dichroic (two-layered) or trichroic (three-layered) polymer tube (parison) is formed by coextrusion of a polyamide layer and a polyamide elastomer layer; a step 2 in which the parison is stretched in the axial direction at a temperature within a range from a secondary transition temperature to a primary transition temperature of both the polymers, and the stretched parison is biaxially stretched by being caused to expand in the radial direction; and a step 3 in which the expanded parison is cooled to a temperature equal to or lower than the secondary transition temperature of both the polymers to form a biaxially stretched balloon including a cylindrical membranous body that has a practically uniform inner diameter, tapered portions that are respectively disposed in the front and back of the membranous body, and connection portions that are respectively disposed in the front and back of the tapered portions and connected to a catheter.

Each of these steps is described below in more detail.

Step 1

The step 1 in which a tube-like parison is formed of a stretchable polymer can be performed by a general-purpose extruder equipped with a die.

The polyamide elastomer, which is obtained by polymerizing a polyamide elastomer by the method described above by melt polymerization, or the polyamide elastomer itself having not undergone polymerization, and polyamide are used as polymers for molding. The polymers for molding are respectively heated and melted in the extruder and subjected to coextrusion to form a tube-like parison 27 by the die.

The temperature at the time of the extrusion molding is not particularly limited as long as the polymers can be melted. However, the temperature is preferably 180° C. to 300° C. and more preferably 200° C. to 280° C.

Step 2

Figure 2:
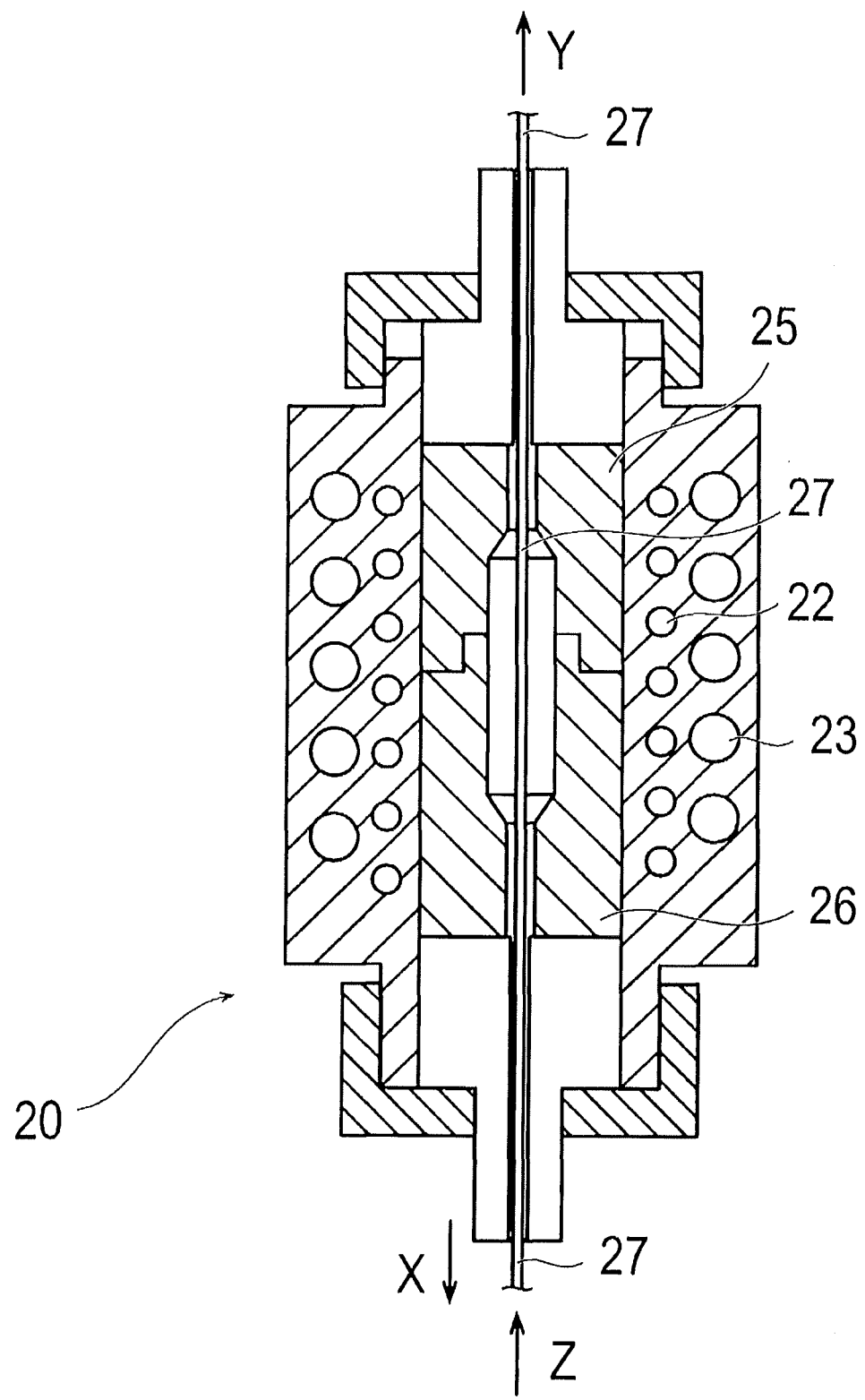
FIG. 2 is a schematic illustration of a mold for molding the catheter balloon disclosed here.

Then, the tube 27 is put into a mold 20 shown in FIG. 2, and one end of the tube 27 is blocked.

The blocking is performed by heating and melting or sealing by high frequency or by using a clamp or the like.

FIG. 2 is a cross-sectional view of the mold 20 for molding a balloon. The mold 20 includes heaters 22 as heating means for heating and cooling tubes 23 as cooling means for cooling.

Moreover, the mold 20 consists of separable molds 25 and 26. The shape of the inner surface that is formed when the separable molds 25 and 26 are combined with each other becomes the basic shape of the outer surface of the balloon to be formed.

Subsequently, as shown in FIG. 2, the heaters 22 are operated such that the tube 27 in the portion for forming a balloon 11 is heated at a temperature within a range from a secondary transition temperature to a primary transition temperature of the polymers (the polyamide and polyamide elastomer that form the tube 27), specifically, at a temperature slightly exceeding the secondary transition temperature.

While being kept in a heated state, the tube 27 is stretched in the direction of the arrows X and Y. Moreover, gas is supplied in a pressurized state into the tube 27 in the direction of the arrow Z, such that the tube 27 of the heated portion in the mold 20 is caused to come into close contact with the inner wall surface of the separable molds 25 and 26.

Step 3

Thereafter, a coolant is circulated inside a cooling tube 23 to cool the tube 27 to a temperature equal to or lower than the secondary transition temperature.

The tube may be naturally cooled simply by being left as is without performing circulation of the coolant.

Then, the internal pressure of the tube 27 is controlled to be normal pressure, and then the tube 27 is pulled out of the mold 20.

Subsequently, the distal end portion and the proximal end portion of the tube 27 is cut, whereby the basic shape of a balloon as shown in FIG. 1 is formed.

The above stretching treatment may be performed twice or more to form a balloon having a desired thickness.

As a preferable embodiment, the balloon catheter disclosed here will be described below, but the invention here is not limited to the following embodiment.

In the following description and reference to various drawing figures, the same features are designated by the same reference numerals.

In addition, the dimensional ratio of the drawings has been exaggerated for the convenience of description and may be different from the actual ratio in some cases.

Figure 3:
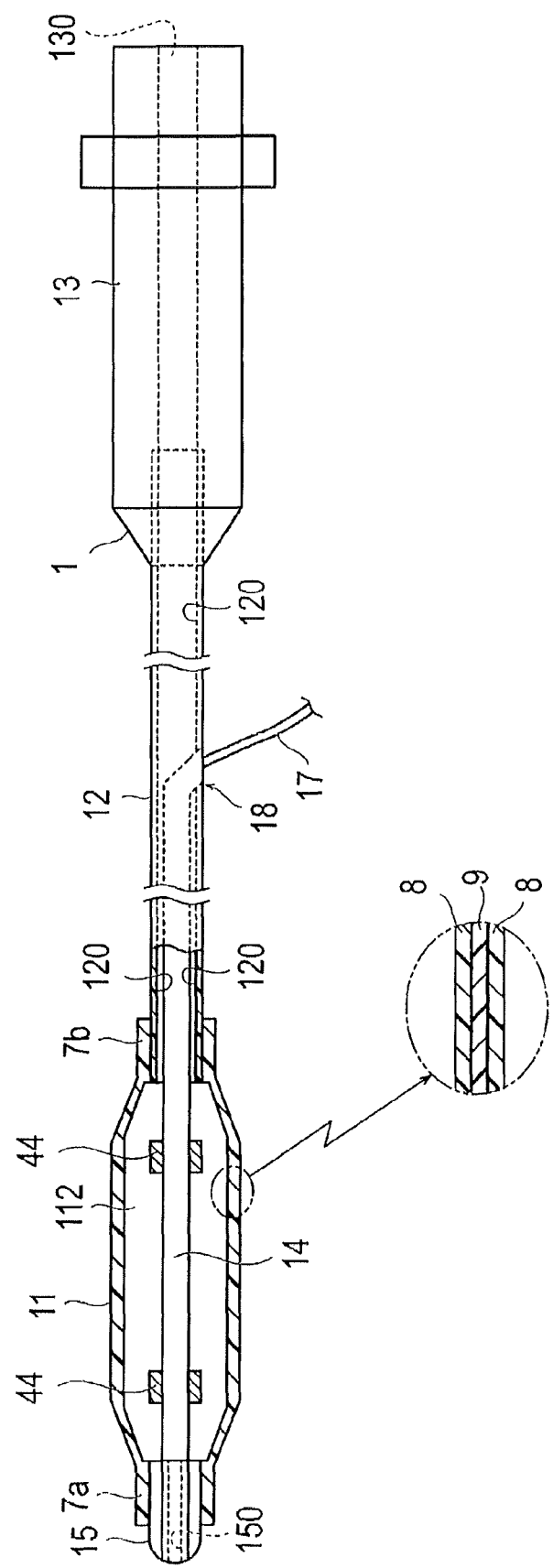
FIG. 3 is a somewhat schematic partial longitudinal cross-section view of an example of a balloon catheter disclosed here.
Figure 5C:
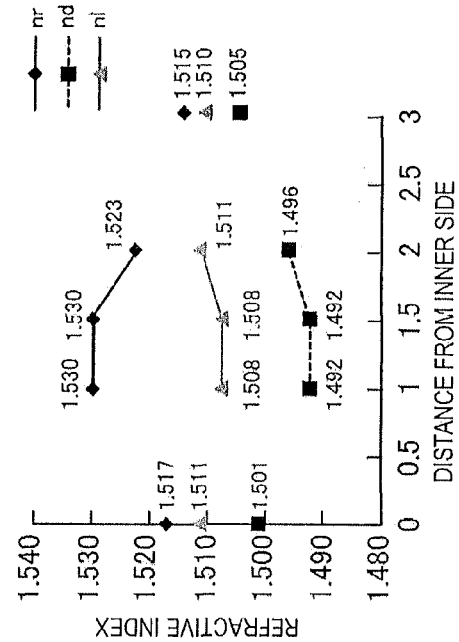
FIGS. 5(a), 5(b) and 5(c) show experimental data of examples of the catheter disclosed here.
Figure 5A:
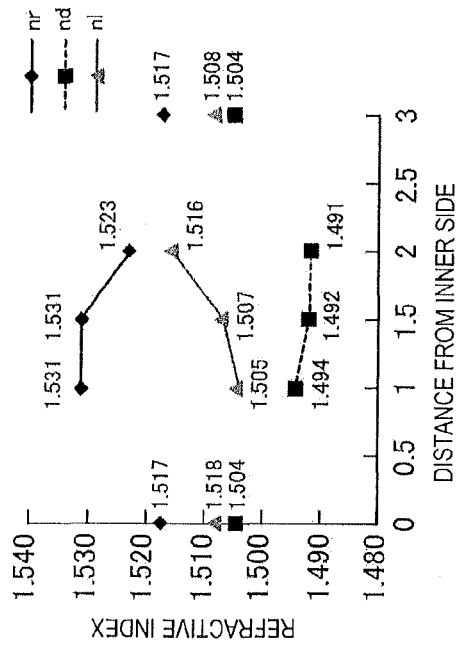
Figure 5B:
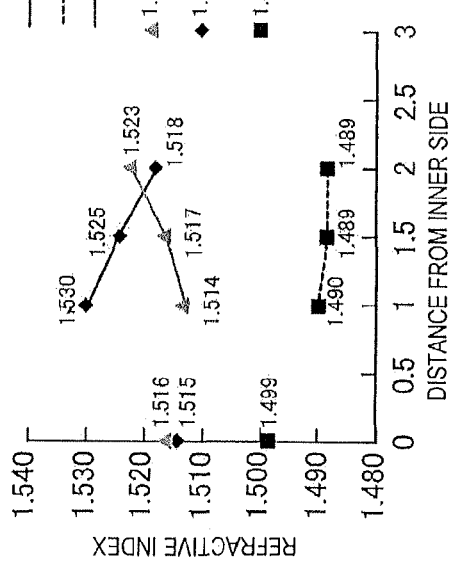

FIG. 3 schematically illustrates an example of the balloon catheter disclosed here. In FIG. 3, a three-layer lamination-type balloon shown in FIG. 1B is described as an example of the balloon 11. However, a balloon having a two-layer structure such as shown in FIG. 1A, or other balloons consistent with the disclosure here, can also be used, and so the balloon catheter is not limited to the one described and illustrated here.

As shown in FIG. 3, a balloon catheter 10 includes a catheter body 1 that has a long outer tube 12 being able to transport fluid, the balloon 11 that is connected to the distal end of the catheter body 1, and a hub 13 that is mounted on the proximal end of the catheter body 1.

The catheter body 1 also includes an inner tube 14 that passes through a lumen 120 formed inside the outer tube 12 and a distal end member 15 that is disposed at the distal end of the inner tube 14.

The distal end refers to an end portion positioned at the side to be inserted into the blood vessel at the time of use, and the proximal end refers to an end portion positioned at the side of an operator who operates the balloon catheter 10 at the time of use.

FIG. 3 shows a rapid exchange-type catheter in which a single lumen is formed at the side of the proximal end portion of the catheter and which includes a wire port into which a guide wire is inserted between the distal end and the proximal end wire port. However, the catheter may be an over-the-wire type in which a double-lumen may be formed around the same axis at the side of the proximal end portion of the catheter, and the inner tube extends to the hub.

The balloon catheter 10 is an example applied to a vasodilating catheter. The balloon and the balloon catheter disclosed here can also be applied to other catheters such as a urethral catheter.

Examples of the fluid supplied into the balloon from the catheter include known substances such as contrast media, helium gas, a physiological salt solution, $CO_2$ gas, $O_2$ gas, $N_2$ gas, and the air.

The structure of the balloon catheter 10 disclosed here will be described in more detail. As shown in FIG. 3, the balloon catheter 10 includes the inner tube 14 that has a first lumen 150 having an open distal end; the outer tube 12 that is disposed in a position, which is spaced from the distal end of the inner tube 14 toward the proximal end by a predetermined length, while sharing the same axis with the inner tube 14 (i.e., the inner tube 14 and the outer tube 12 are coaxial) and forming the second lumen 120 between the outer tube 12 and the outer surface of the inner tube 14; the foldable balloon 1 that has a connection portion (at the side of distal end portion of the balloon) 7a connected to and mounted on the inner tube 14 and a connection portion (at the side of proximal end portion of the balloon) 7b connected to and mounted on the outer tube 12, and is communicated with the second lumen 120 near the proximal end portion; and the hub 13 that includes an opening portion communicated with the second lumen.

The balloon catheter 10 is constituted by the catheter balloon body 1, which includes the inner tube 14 and the outer tube 12, the hub 13, and the balloon 11.

The inner tube 14 includes a first lumen 150 (outer lumen at the inner side) having an opened distal end.

The first lumen 150 is a lumen for inserting a guide wire and communicates with a wire port 18 as an opening portion forming a guide wire port.

A guide wire 17 can be inserted through the wire port 18.

The outer diameter of the inner tube 14 is 0.30 mm to 2.50 mm, preferably 0.40 mm to 2.00 mm, and the inner diameter of the inner tube 14 is 0.20 mm to 2.35 mm, preferably 0.25 mm to 1.70 mm.

It is preferable for the material forming the inner tube 14 to be flexible to some extent. For example, polyolefins such as polyethylene, polypropylene, an ethylene-propylene copolymer, and an ethylene-vinyl acetate copolymer, and thermoplastic resins such as polyvinyl chloride, polyurethane, polyamide, polyamide elastomer, and polyester elastomer can be used.

Into the outer tube 12, the inner tube 14 is inserted or positioned. The distal end of the outer tube 12 is placed in a position that slightly recedes (is slightly proximal) from the distal end of the inner tube. The second lumen 120 is formed by or between the inner surface of the outer tube 12 and the outer surface of the inner tube 14.

Accordingly, the second lumen 120 is a lumen having a sufficient volume.

Moreover, the distal end of the second lumen 120 communicates with the inside of the aforementioned balloon 11 in the distal end portion of the balloon. The proximal end of the second lumen 120 communicates with an opening portion 130 of the hub 13 that forms an injection port for injecting fluid (for example, contrast media, helium gas, a physiological salt solution, $CO_2$ gas, or $O_2$ gas) for expanding the balloon.

The outer diameter of the outer tube 12 is 0.50 mm to 4.30 mm, preferably 0.60 mm to 4.00 mm, and the inner diameter of the outer tube 12 is 0.40 mm to 3.80 mm, preferably 0.50 mm to 3.00 mm.

In addition, the aforementioned radiopaque substances may be optionally injected into the balloon at the time of balloon dilation.

It is preferable for the material for forming the outer tube 12 to be flexible to some extent. For example, polyolefins such as polyethylene, polypropylene, an ethylene-propylene copolymer, and an ethylene-vinyl acetate copolymer and thermoplastic resins such as polyvinyl chloride, polyurethane, polyamide, polyamide elastomer, and polyester elastomer can be used.

In FIG. 3, it is preferable that the distal end of the balloon catheter 10 be provided with the distal end member 15 having a spherical surface that plays a role of assisting the catheter to move along the blood vessel and prevents the blood vessel wall from being damaged.

The balloon 11 is foldable. When the balloon is not dilated, the balloon can be folded around the outer periphery of the inner tube 14.

Moreover, the balloon 11 is a foldable balloon having a cylindrical body with practically uniform diameter, in which at least a portion of the cylindrical body has a cylindrical shape so as to rather easily dilate stenosed portions of blood vessels or body cavities.

In addition, the connection portion 7b of the balloon 11 is fixed in a liquid-tight manner to the distal end portion of the outer tube 12 by an adhesive or heat-sealing.

The connection portion 7a is also fixed in a liquid-tight manner to the distal end portion of the inner tube 14 in the same manner as described above.

As shown in FIG. 3, in the balloon 11, a space 112 is formed between the inner surface of the balloon 11 and the outer surface of the inner tube 14 at the time of dilation.

The entire circumference of the proximal end of the space 112 is communicated with the second lumen 120.

As described above, since the proximal end of the balloon 11 communicates with the second lumen having a relatively large volume, it is rather easy to inject fluid into the balloon 11 from the second lumen.

The balloon 11 forming a part of the balloon catheter shown in FIG. 3 is the balloon described above.

In FIG. 3, the balloon 11 is constituted with three layers. However, the configuration or constitution of the balloon is not limited in this regard, as long as the balloon is constituted with at least two or more layers including the polyamide layer and the polyamide elastomer layer as described above.

In order to make it possible to confirm the position of the cylindrical membranous body of the balloon 11 by radiography, it is preferable to place one or more X-ray markers 44 on the outer surface of the inner tube 14.

As shown in FIG. 3, it is preferable that the X-ray markers 44 be placed in a position that is closer to the proximal end of the balloon 11 than to the portion where the balloon 11 is fixed to the inner tube 14 and a position that is closer to the distal end of the balloon 11 than to the portion where the balloon is fixed to the outer tube 12. In other words, it is preferable that the markers be placed at sites positioned in both ends of the cylindrical membranous body 2 of the balloon 11.

It is preferable for the X-ray markers 44 to be formed of a radiopaque substance (for example, gold, platinum, iridium, tungsten, or an alloy of these).

The hub 13 includes the opening portion 130 which is communicated with the second lumen 120 and forms an injection port as an inlet of a path through which fluid is injected or discharged.

Accordingly, the opening portion 130 plays a role of a flow path and is communicated with a portion for supplying and discharging fluid, for example, an indeflator, a syringe, or a pump.

In this manner, fluid is supplied to the balloon 11 through the opening portion 130 and the second lumen 120 and discharged out of the balloon 11.

That is, the opening portion 130 and the lumen 120 function as a pathway for supplying and discharging drive fluid which causes the balloon 11 to dilate or contract.

As materials for forming the hub, thermoplastic resins such as polycarbonate, polyamide, polysulfone, polyarylate, and a methacrylate-butylene-styrene copolymer can be preferably used.

EXAMPLES

Hereinafter, specific examples of the catheter balloon will be described.

Example 1

A polyamide elastomer (melt viscosity of 1,260 Pa·s) resin (PAE1) which was obtained by performing melt polymerization on polyamide elastomer (Grilamide ELG5660 manufactured by EMS-GRIVORY, shore D hardness of 56) was prepared, and a three-layered tube (magnification of inner diameter expansion; 8.2-fold, ϕ0.37×0.47× 0.82×0.88 mm) using PAE1 for the inner and outer layers and polyamide (Grilamide L25 manufactured by EMS-GRIVORY) for the interlayer was molded.

Thereafter, dry nitrogen was blown into the obtained tube for 30 seconds at a pressure of 3.9 MPa at 110° C. to perform blow molding, thereby preparing a balloon having an outer diameter of 3.00 mm and a thickness of 22.4 μm. A withstanding pressure (burst pressure of the balloon) was 37.1 atm, and a compliance thereof was 0.010 mm/atm.

The term "compliance" as used here indicates how easily the diameter expands and is represented by the slope of a compliance curve that shows the relationship established between pressure and the increase in the outer diameter of the balloon when internal pressure in an operation range of 12 atm to 22 atm is applied to the balloon.

The obtained balloon was cut into slices and cut in the long-axis direction. The cross-section of the balloon was observed with a polarization microscope, and retardation at five sites shown in FIG. 4(a) was measured to calculate the birefringence.

As a result of assigning the calculated birefringence to the aforementioned Equations (1) to (3), the refractive index $n_{r1}$ in the circumferential direction of the surface of inner side of the polyamide layer as the interlayer was 1.532, and the refractive index $n_{r2}$ in the circumferential direction of the surface of inner side of the polyamide elastomer layer as the inner layer was 1.517.

FIGS. 4(a) and 4(b) show the sites for measuring each of the refractive indices in Examples and Comparative examples.

For the balloon formed of the three-layered membrane, retardation was measured in each of five sites shown in FIG. 4(a). For the balloon formed of two-layered membrane, retardation was measured in each of four sites shown in FIG. 4(b).

Moreover, the graphs of Examples and Comparative examples shown in FIGS. 4(c), 4(d), 5(a), 5(b), 5(c), 6(a), 6(b), 7(a), 7(b), 8(a), 8(b), 8(c) and 8(d) show the relationship between the position of the five or four sites in the balloon and the refractive indices in those positions. $n_r$ indicates a refractive index in the circumferential direction, $n_l$ indicates a refractive index in the long-axis direction, and $n_d$ indicates a refractive index in the thickness direction.

That is, as shown in FIG. 4(a), for the balloon formed of three-layered membrane, five sites in total, which include a site that is assigned with 0 and corresponds to the vicinity of the surface of inner side of the polyamide elastomer layer forming the innermost circumference of the cross-section of the catheter balloon, a site that is assigned with 1 and corresponds to the vicinity of the inner side surface of the polyamide layer adjacent to the polyamide elastomer layer as the innermost circumference, a site that is assigned with 2 and corresponds to the vicinity of the outer side surface of the polyamide layer, a site that is assigned with 1.5 and interposed between the inner side surface and the outer side surface of the polyamide layer, and a site that is assigned with 3 and corresponds to the vicinity of the outer side surface of the polyamide elastomer layer forming the outermost circumference of the cross-section of the catheter balloon, are defined as distances from the inner circumferential surface of the catheter balloon of Examples 1 to 9 and Comparative examples 1 and 2.

Moreover, as shown in FIG. 4(b), for the balloon formed of two-layered membrane, four sites in total, which include a site that is assigned with 0 and corresponds to the vicinity of the inner side surface of the polyamide layer forming the innermost circumference of the cross-section of the balloon, a site that is assigned with 1 and corresponds to the vicinity of the outer side surface of the polyamide layer, a site that is assigned with 1.5 and interposed between the inner side surface and the outer side surface of the polyamide layer, and a site that is assigned with 2 and corresponds to the vicinity of the outer side surface of the polyamide elastomer layer forming the outermost circumference of the cross-section of the catheter balloon, are defined as distances from the inner circumferential surface of the catheter balloon of Comparative examples 3 and 4.

Example 2

A polyamide elastomer (melt viscosity of 1,260 Pa·s) resin (PAE1) which was obtained by performing melt polymerization on polyamide elastomer (Grilamide ELG5660 manufactured by EMS-GRIVORY, shore D hardness of 56) was prepared, and a three-layered tube (magnification of inner diameter expansion; 8.6-fold, ϕ0.35×0.46× 0.77×0.83 mm) using PAE1 for the inner and outer layers and polyamide (Grilamide L25 manufactured by EMS-GRIVORY) for the interlayer was molded.

Thereafter, dry nitrogen was blown into the obtained tube for 120 seconds at a pressure of 3.9 MPa at 110° C. to perform blow molding, thereby preparing a balloon having an outer diameter of 3.00 mm and a thickness of 22.1 μm. A withstanding pressure (burst pressure of the balloon) was 36.8 atm, and a compliance thereof was 0.010 mm/atm.

The obtained balloon was cut into slices and cut in the long-axis direction. The cross-section of the balloon was observed with a polarization microscope, and retardation at five sites shown in FIG. 4(a) was measured to calculate the birefringence.

As a result of assigning the calculated birefringence to the aforementioned Equations (1) to (3), the refractive index $n_{r1}$ in the circumferential direction of the surface of inner side of the polyamide layer as the interlayer was 1.533, and the refractive index $n_{r2}$ in the circumferential direction of the surface of inner side of the polyamide elastomer layer as the inner layer was 1.520.

Example 3

A polyamide elastomer (melt viscosity of 3,489 Pa·s) resin (PAE1) which was obtained by performing melt polymerization on polyamide elastomer (Grilamide ELG5660 manufactured by EMS-GRIVORY, shore D hardness of 56) was prepared, and a three-layered tube (magnification of inner diameter expansion; 8.6-fold, ϕ0.35ϕ0.47× 0.82×0.88 mm) using PAE1 for the inner and outer layers and polyamide (Grilamide L25 manufactured by EMS-GRIVORY) for the interlayer was molded.

Thereafter, dry nitrogen was blown into the obtained tube for 30 seconds at a pressure of 4.0 MPa at 100° C. to perform blow molding, thereby preparing a balloon having an outer diameter of 3.00 mm and a thickness of 22.6 μm. A withstanding pressure (burst pressure of the balloon) was 32.7 atm, and a compliance thereof was 0.009 mm/atm.

The obtained balloon was cut into slices and cut in the long-axis direction. The cross-section of the balloon was observed with a polarization microscope, and retardation at five sites shown in FIG. 4(a) was measured to calculate the birefringence.

As a result of assigning the calculated birefringence to the aforementioned Equations (1) to (3), the refractive index $n_{r1}$ in the circumferential direction of the surface of inner side of the polyamide layer as the interlayer was 1.531, and the refractive index $n_{r2}$ in the circumferential direction of the surface of inner side of the polyamide elastomer layer as the inner layer was 1.517.

Example 4

A polyamide elastomer (melt viscosity of 5,282 Pa·s) resin (PAE1) which was obtained by performing melt polymerization on polyamide elastomer (Grilamide ELG6260 manufactured by EMS-GRIVORY, shore D hardness of 62) was prepared, and a three-layered tube (magnification of inner diameter expansion; 8.6-fold, φ0.35×0.47× 0.82×0.88 mm) using PAE1 for the inner and outer layers and polyamide (Grilamide L25 manufactured by EMS-GRIVORY) for the interlayer was molded.

Thereafter, dry nitrogen was blown into the obtained tube for 120 seconds at a pressure of 3.7 MPa at 110° C. to perform blow molding, thereby preparing a balloon having an inner diameter of 3.00 mm and a thickness of 22.8 μm. A withstanding pressure (burst pressure of the balloon) was 29.9 atm, and a compliance thereof was 0.011 mm/atm.

The obtained balloon was cut into slices and cut in the long-axis direction. The cross-section of the balloon was observed with a polarization microscope, and retardation at five sites shown in FIG. 4(a) was measured to calculate the birefringence.

As a result of assigning the calculated birefringence to the aforementioned Equations (1) to (3), the refractive index $n_{r1}$ in the circumferential direction of the surface of inner side of the polyamide layer as the interlayer was 1.530, and the refractive index $n_{r2}$ in the circumferential direction of the surface of inner side of the polyamide elastomer layer as the inner layer was 1.516.

Example 5

A polyamide elastomer (melt viscosity of 5,282 Pa·s) resin (PAE1) which was obtained by performing melt polymerization on polyamide elastomer (Grilamide ELG6260 manufactured by EMS-GRIVORY, shore D hardness of 62) was prepared, and a three-layered tube (magnification of inner diameter expansion; 7.7-fold, φ0.39×0.50× 0.82×0.92 mm) using PAE1 for the inner and outer layers and polyamide (Grilamide L25 manufactured by EMS-GRIVORY) for the interlayer was molded.

Thereafter, dry nitrogen was blown into the obtained tube for 30 seconds at a pressure of 3.2 MPa at 130° C. to perform blow molding, thereby preparing a balloon having an outer diameter of 3.00 mm and a thickness of 21.9 μm. A withstanding pressure (burst pressure of the balloon) was 28.1 atm, and a compliance thereof was 0.010 mm/atm.

The obtained balloon was cut into slices and cut in the long-axis direction. The cross-section of the balloon was observed with a polarization microscope, and retardation at five sites shown in FIG. 4(a) was measured to calculate the birefringence.

As a result of assigning the calculated birefringence to the aforementioned Equations (1) to (3), the refractive index $n_{r1}$ in the circumferential direction of the surface of inner side of the polyamide layer as the interlayer was 1.530, and the refractive index $n_{r2}$ in the circumferential direction of the surface of inner side of the polyamide elastomer layer as the inner layer was 1.517.

Example 6

A polyamide elastomer (melt viscosity of 7,391 Pa·s) resin (PAE1) which was obtained by performing melt polymerization on polyamide elastomer (Grilamide ELG6260 manufactured by EMS-GRIVORY, shore D hardness of 62) was prepared, and a three-layered tube (magnification of inner diameter expansion; 8.6-fold, φ0.35×0.47× 0.82×0.88 mm) using PAE1 for the inner and outer layers and polyamide (Grilamide L25 manufactured by EMS-GRIVORY) for the interlayer was molded.

Thereafter, dry nitrogen was blown into the obtained tube for 30 seconds at a pressure of 3.6 MPa at 110° C. to perform blow molding, thereby preparing a balloon having an outer diameter of 3.00 mm and a thickness of 22.2 μm. A withstanding pressure (burst pressure of the balloon) was 30.9 atm, and a compliance thereof was 0.011 mm/atm.

The obtained balloon was cut into slices and cut in the long-axis direction. The cross-section of the balloon was observed with a polarization microscope, and retardation at five sites shown in FIG. 4(a) was measured to calculate the birefringence.

As a result of assigning the calculated birefringence to the aforementioned Equations (1) to (3), the refractive index $n_{r1}$ in the circumferential direction of the surface of inner side of the polyamide layer as the interlayer was 1.531, and the refractive index $n_{r2}$ in the circumferential direction of the surface of inner side of the polyamide elastomer layer as the inner layer was 1.517.

Example 7

A three-layered tube (magnification of inner diameter expansion; 8.5-fold, φ0.36×0.50×0.84×0.88 mm) using polyamide elastomer (Grilamide ELG5660 manufactured by EMS-GRIVORY, shore D hardness of 56) for the inner and outer layers and polyamide (Grilamide L25 manufactured by EMS-GRIVORY) for the interlayer was molded.

Thereafter, dry nitrogen was blown into the obtained tube for 30 seconds at a pressure of 4.2 MPa at 90° C. to perform blow molding, thereby preparing a balloon having an outer diameter of 3.00 mm and a thickness of 20.4 μm. A withstanding pressure (burst pressure of the balloon) was 33.1 atm, and a compliance thereof was 0.013 mm/atm.

The obtained balloon was cut into slices and cut in the long-axis direction. The cross-section of the balloon was observed with a polarization microscope, and retardation at five sites shown in FIG. 4(a) was measured to calculate the birefringence.

As a result of assigning the calculated birefringence to the aforementioned Equations (1) to (3), the refractive index $n_{r1}$ in the circumferential direction of the surface of inner side of the polyamide layer as the interlayer was 1.526, and the refractive index $n_{r2}$ in the circumferential direction of the surface of inner side of the polyamide elastomer layer as the inner layer was 1.514.

Example 8

A three-layered tube (magnification of inner diameter expansion; 8.2-fold, φ0.37×0.51×0.84×0.88 mm) using polyamide elastomer (Grilamide ELG5660 manufactured by EMS-GRIVORY, shore D hardness of 56) for the inner and outer layers and polyamide (Grilamide L25 manufactured by EMS-GRIVORY) for the interlayer was molded.

Thereafter, dry nitrogen was blown into the obtained tube for 30 seconds at a pressure of 4.2 MPa at 90° C. to perform blow molding, thereby preparing a balloon having an outer diameter of 3.00 mm and a thickness of 19.6 μm. A withstanding pressure (burst pressure of the balloon) was 33.3 atm, and a compliance thereof was 0.016 mm/atm.

The obtained balloon was cut into slices and cut in the long-axis direction. The cross-section of the balloon was observed with a polarization microscope, and retardation at five sites shown in FIG. 4(a) was measured to calculate the birefringence.

As a result of assigning the calculated birefringence to the aforementioned Equations (1) to (3), the refractive index $n_{r1}$ in the circumferential direction of inner side of the polyamide layer as the interlayer was 1.528, and the refractive index $n_{r2}$ in the circumferential direction of the surface of inner side of the polyamide elastomer layer as the inner layer was 1.513.

Example 9

A three-layered tube (magnification of inner diameter expansion; 7.9-fold, ϕ0.38×0.52×0.85×0.89 mm) using polyamide elastomer (Grilamide ELG5660 manufactured by EMS-GRIVORY, shore D hardness of 56) for the inner and outer layers and polyamide (Grilamide L25 manufactured by EMS-GRIVORY) for the interlayer was molded.

Thereafter, dry nitrogen was blown into the obtained tube for 30 seconds at a pressure of 4.0 MPa at 100° C. to perform blow molding, thereby preparing a balloon having an outer diameter of 3.00 mm and a thickness of 19.4 µm. A withstanding pressure (burst pressure of the balloon) was 33.0 atm, and a compliance thereof was 0.015 mm/atm.

The obtained balloon was cut into slices and cut in the long-axis direction. The cross-section of the balloon was observed with a polarization microscope, and retardation at five sites shown in FIG. 4(a) was measured to calculate the birefringence.

As a result of assigning the calculated birefringence to the aforementioned Equations (1) to (3), the refractive index $n_{r1}$ in the circumferential direction of inner side of the polyamide layer as the interlayer was 1.525, and the refractive index $n_{r2}$ in the circumferential direction of the surface of inner side of the polyamide elastomer layer as the inner layer was 1.515.

Comparative Example 1

A three-layered tube (magnification of inner diameter expansion; 8.2-fold, ϕ0.37×0.48×0.82×0.90 mm) using polyamide elastomer (PEBAX5533 manufactured by ARUKEMA K.K., shore D hardness of 55) for the inner and outer layers and polyamide (Grilamide L25 manufactured by EMS-GRIVORY) for the interlayer was molded.

Thereafter, dry nitrogen was blown into the obtained tube for 30 seconds at a pressure of 3.0 MPa at 110° C. to perform blow molding, thereby preparing a balloon having an outer diameter of 3.00 mm and a thickness of 22.3 µm. A withstanding pressure (burst pressure of the balloon) was 26.0 atm, and a compliance thereof was 0.018 mm/atm.

The obtained balloon was cut into slices and cut in the long-axis direction. The cross-section of the balloon was observed with a polarization microscope, and retardation at five sites shown in FIG. 4(a) was measured to calculate the birefringence.

As a result of assigning the calculated birefringence to the aforementioned Equations (1) to (3), the refractive index $n_{r1}$ in the circumferential direction of the surface of inner side of the polyamide layer as the interlayer was 1.528, and the refractive index $n_{r2}$ in the circumferential direction of the surface of inner side of the polyamide elastomer layer as the inner layer was 1.522.

Comparative Example 2

A three-layered tube (magnification of inner diameter expansion; 8.6-fold, ϕ0.35×0.47×0.82×0.88 mm) using polyamide elastomer (Grilamide ELG5930 manufactured by EMS-GRIVORY, shore D hardness of 59) for the inner layer, polyamide (Grilamide L25 manufactured by EMS-GRIVORY) for the interlayer, and polyamide elastomer (Grilamide ELG5660 manufactured by EMS-GRIVORY, shore D hardness of 56) for the outer layer was molded.

Thereafter, dry nitrogen was blown into the obtained tube for 30 seconds at a pressure of 4.2 MPa at 90° C. to perform blow molding, thereby preparing a balloon having an outer diameter of 3.00 mm and a thickness of 23.2 µm. A withstanding pressure (burst pressure of the balloon) was 21.3 atm, and a compliance thereof was 0.015 mm/atm.

The obtained balloon was cut into slices and cut in the long-axis direction. The cross-section of the balloon was observed with a polarization microscope, and retardation at five sites shown in FIG. 4(a) was measured to calculate the birefringence.

As a result of assigning the calculated birefringence to the aforementioned Equations (1) to (3), the refractive index $n_{r1}$ in the circumferential direction of the surface of inner side of the polyamide layer as the interlayer was 1.532, and the refractive index $n_{r2}$ in the circumferential direction of the surface of inner side of the polyamide elastomer layer as the inner layer was 1.527.

Comparative Example 3

The cross-section of a balloon Hiryu (ϕ3.00 mm×15 mm, membrane thickness of 19.8 µm, withstanding pressure of 28.0 atm, compliance of 0.016 mm/atm) manufactured by Terumo Corporation (two-layered balloon constituted with an inner layer formed of polyamide and an outer layer formed of polyamide elastomer) was observed with a polarization microscope, and retardation at four sites shown in FIG. 4(a) was measured. As a result, a refractive index ($n_r$) in the circumferential direction of the surface of inner side of the polyamide layer was 1.531, and $n_r$ of the surface of innermost layer where polyamide elastomer did not exist was less than 1.520.

Comparative Example 4

The cross-section of a balloon Kongou (ϕ3.00 mm×15 mm, membrane thickness of 23.4 µm, withstanding pressure of 27.9 atm, compliance of 0.015 mm/atm) manufactured by Terumo Corporation (two-layered balloon constituted with an inner layer formed of polyamide and an outer layer formed of polyamide elastomer) was observed with a polarization microscope, and retardation at four sites shown in FIG. 4(a) was measured. As a result, a refractive index ($n_r$) in the circumferential direction in the surface of inner side of the polyamide layer was 1.529, and $n_r$ of the surface of the innermost layer where polyamide elastomer did not exist was less than 1.520.

Experimental data showing the relationship between the respective refractive indices of Examples 1 to 9 as well as Comparative examples 1 to 4 and the distance from the inner circumferential surface of the balloon are shown in FIG. 4(b) to FIG. 8.

The refractive index $n_r$ in the circumferential direction of Examples 1 to 9 and Comparative examples 1 to 4 are shown below.

TABLE 1

| | nr2 of surface of inner side of inner layer (A) | nr1 of surface of inner side of inter layer (B) | (B) − (A) |
|---|---|---|---|
| Example 1 | 1.517 | 1.532 | 0.015 |
| Example 2 | 1.520 | 1.533 | 0.013 |
| Example 3 | 1.517 | 1.531 | 0.014 |
| Example 4 | 1.516 | 1.530 | 0.014 |
| Example 5 | 1.517 | 1.530 | 0.013 |
| Example 6 | 1.517 | 1.531 | 0.014 |
| Example 7 | 1.514 | 1.526 | 0.012 |
| Example 8 | 1.513 | 1.528 | 0.015 |
| Example 9 | 1.515 | 1.525 | 0.010 |
| Comparative example 1 | 1.522 | 1.528 | 0.006 |
| Comparative example 2 | 1.527 | 1.532 | 0.005 |
| Comparative example 3 | No PAE layer | 1.531 | Failure of calculation |
| Comparative example 4 | No PAE layer | 1.529 | Failure of calculation |

The detailed description above describes a catheter balloon and a balloon catheter disclosed by way of example. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A cylindrical catheter balloon possessing an axis and formed of a membrane comprised of a laminate of at least two layers, one of the layers being a polyamide elastomer layer and the other layer being a polyamide layer, the polyamide layer possessing an inner side, the polyamide elastomer layer being disposed at the inner side of the polyamide layer, a refractive index $n_{r1}$ in a circumferential direction of a cross-section perpendicular to the axis in an inner side surface of the polyamide layer is greater than a refractive index $n_{r2}$ in the circumferential direction of a cross-section perpendicular to the axis in an inner side surface of the polyamide elastomer layer, and a difference between the refractive index $n_{r1}$ and the refractive index $n_{r2}$ is 0.01 to 0.02, and wherein a refractive index in a radial direction of the cross-section perpendicular to the axis in the inner side surface of the polyamide elastomer layer is greater than a refractive index of the polyamide layer.

2. The cylindrical catheter balloon according to claim 1, wherein the refractive index $n_{r2}$ in the circumferential direction of the cross-section perpendicular to the axis in the inner side surface of the polyamide elastomer layer is 1.520 or less.

3. The cylindrical catheter balloon according to claim 2, wherein the cylindrical catheter balloon possesses opposite ends that are both open.

4. The cylindrical catheter balloon according to claim 2, wherein the refractive index $n_{r1}$ in the circumferential direction of the cross-section perpendicular to the axis in the inner side surface of the polyamide layer is 1.520 to 1.540.

5. The cylindrical catheter balloon according to claim 4, further comprising one more polyamide elastomer layer disposed at an outer side of the polyamide layer so that the polyamide layer is positioned between respective polyamide elastomer layers.

6. The cylindrical catheter balloon according to claim 2, further comprising one more polyamide elastomer layer disposed at an outer side of the polyamide layer so that the polyamide layer is positioned between respective polyamide elastomer layers.

7. The cylindrical catheter balloon according to claim 1, wherein the refractive index $n_{r1}$ in the circumferential direction of the cross-section perpendicular to the axis in the inner side surface of the polyamide layer is 1.520 to 1.540.

8. The cylindrical catheter balloon according to claim 1, further comprising one more polyamide elastomer layer disposed at an outer side of the polyamide layer so that the polyamide layer is positioned between respective polyamide elastomer layers.

9. The cylindrical catheter balloon according to claim 1, wherein the cylindrical catheter balloon possesses opposite ends that are both open.

10. A balloon catheter comprising the catheter balloon according to claim 1.

11. The cylindrical catheter balloon according to claim 1, wherein the difference between the refractive index $n_{r1}$ and the refractive index $n_{r2}$ is 0.01 to 0.015.

12. A balloon catheter comprising:
an outer tube;
an inner tube positioned in the outer tube; and
a balloon possessing a proximal end portion fixed to the outer tube and a distal end portion fixed to the inner tube, the balloon possessing an axis and being a membrane comprised of a laminate of at least two layers, one of the layers being a polyamide elastomer layer and the other layer being a polyamide layer, the polyamide layer possessing an inner side, the polyamide elastomer layer being disposed at the inner side of the polyamide layer, a refractive index $n_{r1}$ in a circumferential direction of a cross-section perpendicular to the axis in an inner side surface of the polyamide layer is greater than a refractive index $n_{r2}$ in the circumferential direction of a cross-section perpendicular to the axis in an inner side surface of the polyamide elastomer layer, and a difference between the refractive index $n_{r1}$ and the refractive index $n_{r2}$ is 0.01 to 0.02, and wherein a refractive index in a radial direction of the cross-section perpendicular to the axis in the inner side surface of the polyamide elastomer layer is greater than a refractive index of the polyamide layer.

13. The balloon catheter according to claim 12, wherein the catheter balloon is a cylindrical catheter balloon.

14. The balloon catheter according to claim 12, wherein the refractive index $n_{r2}$ in the circumferential direction of the cross-section perpendicular to the axis in the inner side surface of the polyamide elastomer layer is 1.520 or less.

15. The balloon catheter according to claim 12, wherein the inner tube extends distally beyond a distal-most end of the catheter balloon, and the outer tube extends proximally beyond a proximal-most end of the catheter balloon.

16. The balloon catheter according to claim 12, wherein the refractive index $n_{r1}$ in the circumferential direction of the cross-section perpendicular to the axis in the inner side surface of the polyamide layer is 1.520 to 1.540.

17. The balloon catheter according to claim 12, wherein the polyamide elastomer layer is a first polyamide elastomer layer, further comprising a second polyamide elastomer layer at an outer side of the polyamide layer so that the polyamide layer is positioned between the first and the second polyamide elastomer layers.

18. The balloon catheter according to claim 12, wherein the difference between the refractive index $n_{r1}$ and the refractive index $n_{r2}$ is 0.01 to 0.015.

* * * * *